(12) United States Patent
Siepe et al.

(10) Patent No.: US 10,240,216 B2
(45) Date of Patent: Mar. 26, 2019

(54) ANTIFUNGAL PENICILLIUM STRAINS, FUNGICIDAL EXTROLITES THEREOF, AND THEIR USE

(71) Applicant: BASF SE, Ludwigshafen (DE)

(72) Inventors: Isabella Siepe, Dossenheim (DE); Thorsten Jabs, Hassloch (DE); Anja Schueffler, Kaiserslautern (DE); Louis Pergaud Sandjo, Longkak-Yaoundé (CM); Heidrun Anke, Mannheim (DE); Eckhard Thines, Mehlingen (DE); Till Opatz, Oberursel (DE)

(73) Assignee: BASF SE, Ludwigshafen (DE)

( * ) Notice: Subject to any disclaimer, the term of this patent is extended or adjusted under 35 U.S.C. 154(b) by 50 days.

(21) Appl. No.: 15/035,638

(22) PCT Filed: Nov. 10, 2014

(86) PCT No.: PCT/EP2014/074165
§ 371 (c)(1),
(2) Date: May 10, 2016

(87) PCT Pub. No.: WO2015/067800
PCT Pub. Date: May 14, 2015

(65) Prior Publication Data
US 2016/0298201 A1    Oct. 13, 2016

(30) Foreign Application Priority Data
Nov. 11, 2013  (EP) ..................................... 13192333

(51) Int. Cl.
| | | |
|---|---|---|
| *C12P 7/42* | (2006.01) | |
| *C12R 1/80* | (2006.01) | |
| *A01N 63/04* | (2006.01) | |
| *C12N 1/14* | (2006.01) | |
| *C12P 1/02* | (2006.01) | |
| *A01N 37/36* | (2006.01) | |
| *C07C 59/46* | (2006.01) | |
| *A01N 37/06* | (2006.01) | |

(52) U.S. Cl.
CPC .............. *C12R 1/80* (2013.01); *A01N 37/06* (2013.01); *A01N 37/36* (2013.01); *A01N 63/04* (2013.01); *C07C 59/46* (2013.01); *C12N 1/14* (2013.01); *C12P 1/02* (2013.01); *C12P 7/42* (2013.01); *C07C 2602/10* (2017.05); *C07C 2602/28* (2017.05)

(58) Field of Classification Search
CPC ........ A01N 37/06; A01N 37/36; A01N 63/04; C07C 2602/10; C07C 2602/28; C07C 59/46; C07C 2102/10; C12N 1/14; C12P 1/02; C12P 7/42; C12R 1/80
See application file for complete search history.

(56) References Cited

U.S. PATENT DOCUMENTS

2012/0282349 A1* 11/2012 Tamagawa ............. A01N 43/42
424/633

FOREIGN PATENT DOCUMENTS

EP          0052366          5/1982

OTHER PUBLICATIONS

Arimoto et al., "Synthesis and Absolute Stereochemistry of Tanzawaic Acid (GS-1302)," Tetrahedron Letters, vol. 39, (1998), pp. 9513-9516.
El-Neketi et al., "Alkaloids and Polyketides from *Penicillium citrinum*, an Endophyte Isolated from the Moroccan Plant *Ceratonia siliqua*," Journal of Natural Products, vol. 76, No. 6, (2013), pp. 1099-1104.
International Preliminary Report on Patentability, issued in PCT/EP2014/074165, dated May 17, 2016.
International Search Report, issued in PCT/EP2014/074165, dated Feb. 17, 2015.
Kobayashi et al., "Absolute Structure, Biosynthesis, and Anti-Microtubule Activity of Phomopsidin, Isolated from a Marine-Derived Fungus *Phomopsis* sp.," Tetrahedron, vol. 59, (2003), pp. 455-459.
Kuramoto et al., "Tanzawaic Acids A, B, C, and D: Inhibitors of Superoxide Anion Production from *Penicillium citrinum*," Chemistry Letters, (1997), pp. 885-886.
Malmstrom et al., "Secondary Metabolites Characteristic of *Penicillium citrinum, Penicillium steckii* and Related Species," Phytochemistry, vol. 54, No. 3, (2000), pp. 301-309.
Masuma et al., "Arohynapenes A and B, New Anticoccidial Agents Produced by *Penicillium* sp.," The Journal of Antibiotics, vol. 47, No. 1, (1994), pp. 46-53.
Sabat and Gupta, "Nutritional Factors Affecting the Antifungal Activity of *Penicillium steckii* of Mangrove Origin," African Journal of Microbiology Research, vol. 4, No. 3, (2010), pp. 126-135.
Sandjo et al., "Tanzawaic Acids I-L: Four New Polyketides from *Penicillium* sp. IBWF104-06," Beilstein Journal of Organic Chemistry, vol. 10, (2014), pp. 251-258.
Tabata et al., "Arohynapene D, a New Anticoccidial Agent Produced by *Penicillium* sp. OF-2295," The Journal of Antibiotics, vol. 48, No. 1, (1995), pp. 83-84.
Tabata et al., "Hynapenes A, B, and C, New Anticoccidial Agents Produced by *Penicillium* sp.," The Journal of Antibiotices, vol. 46, No. 12, (1993), pp. 1849-1850.

* cited by examiner

*Primary Examiner* — Susan M Hanley
(74) *Attorney, Agent, or Firm* — Brinks Gilson & Lione

(57) ABSTRACT

The present invention relates to fungal strains, which are a member of the genus *Penicillium* and have antifungal activity, and to cell-free extracts of said strains, culture media obtainable by culturing said strains and extrolites produced by said strains, all of which have fungicidal activity. The present invention further relates to compositions comprising said strains, extracts, culture media and extrolites, and their uses in the agrochemical field and the field of controlling phytopathogenic fungi in particular.

4 Claims, 1 Drawing Sheet

Specification includes a Sequence Listing.

SEQ ID NO:1

```
cttggtcatt tagaggaagt aaaagtcgta acaaggtttc cgtaggtgaa cctgcggaag    60
gatcattacc gagtgagggc cctctgggtc caacctccca cccgtgttgc acgaacctgt   120
gttgcttcgg cgggcccgcc gccaggccgc cggggggcat ccgcccccgg gtccgcgccc   180
gccgaagccc ccctctgaac gctgtctgaa gttgcagtct gagacaacta gctaaattag   240
ttaaaacttt caacaacgga tctcttggtt ccggcatcga tgaagaacgc agcgaaatgc   300
gataactaat gtgaattgca gaattcagtg aatcatcgag tctttgaacg cacattgcgc   360
cctctggtat tccggagggc atgcctgtcc gagcgtcatt gctgccctca agcacggctt   420
gtgtgttggg ccccgtcccc cccgctccgg gggggacggg cccgaaaggc agcggcggca   480
ccgcgtccgg tcctcgagcg tatgggctt cgtcacccgc tcttgtaggc ccggccggcg   540
ccagccgacc cccaaccttt tatttttct caggttgacc tcggatcagg tagggatacc   600
cgctgaactt aagcatatca ataa                                          624
```

ANTIFUNGAL PENICILLIUM STRAINS, FUNGICIDAL EXTROLITES THEREOF, AND THEIR USE

BIOLOGICAL DEPOSIT

Biological strain IBWF 104-06 was deposited as Accession No. DSM 27859 on Oct. 9, 2013, with Leibniz Institute DSMZ-German Collection of Microorganisms and Cell Cultures, located at Inhoffenstr. 7B, D-38124, Braunschweig, Germany.

The present invention relates to fungal strains, which are a member of the genus *Penicillium* and have antifungal activity, and to cell-free extracts of said strains, culture media obtainable by culturing said strains and extrolites produced by said strains, all of which have fungicidal activity. The present invention further relates to compositions comprising said strains, extracts, culture media and extrolites, and their uses in the agrochemical field and the field of controlling phytopathogenic fungi in particular.

BACKGROUND OF THE INVENTION

Nature still represents the richest source of bioactive compounds which can be attractive for medicine as well as crop science. In both areas, the omnipresent development of resistances creates the need for new active principles which can only partly be covered by chemical synthesis.

The genus *Penicillium* comprises more than 300 species which produce a variety of bioactive compounds. Well-known drug leads from this genus are penicillin antibiotics produced by *P. chrysogenum* and the antifungal metabolite griseofulvin produced by *P. griseofulvum* and *P. patulum*, and several other secondary metabolites have been described from *Penicillium* species.

For instance, *P. citrinum* is known for the production of the mycotoxin metabolite citrinin and EP 0 052 366 describes hypocholesterolemic fermentation products of *Penicillium citrinum* strain ATCC 20606. *Penicillium* sp. FO-2295, a water isolate, was found to produce a series of anticoccidial compounds, designated as arohynapenes A and B [Masuma, et al., Antibiot. 1994, 47, 46-53] as well as arohynapene D [Tabata, et al., J. Antibiot., 1995, 48, 83-84], but these compounds were reported to show no antimicrobial activity in vitro at a concentration of 1 mg/ml against a number of bacteria and fungi. Further, *Penicillium* sp. FO-1611, a soil isolate, was found to produce a series of anticoccidial compounds, designated as hynapenes A, B and C [Tabata, et al., J. Antiblot., 1993, 46, 1849-1853]. These hynapenes were also reported to show antimicrobial activity in vitro at a concentration of 1 mg/ml against a number of bacteria and fungi, including *Pyricularia oryzae*, the anamorph of *Magnaporthe oryzae*.

Tanzawaic acids A, B, C and D have been isolated from *Penicillium citrinium* obtained from the Tanzawa area of Japan, and tanzawaic acids A and B were found to inhibit superoxide anion production in human neutrophils [Kuramoto, et al., Chem. Lett. 1997, 26, 885-886.]. None of tanzawaic acids A, B, C and D was found to show antimicrotubule activity [Kobayashi, et al., Tetrahedron 59 (2003) 455-459]. Tanzawaic acids E and F have been isolated from a *Penicillium steckii* isolate obtained from an unidentified tunicate [Malmstrom, et al., C. Phytochemistry 2000, 54, 301-309]. Tanzawaic acids G and H have been isolated from a *Penicillium citrinium* isolate obtained from the inner stem tissues of the Moroccan plant *Ceratonia siqua* L. [EI-Neketi et al., Journal of natural products, 76(6), 1099-1104. doi: 10.1021/np4001366]. However, neither tanzawaic acids G nor H were found to be active against a number of bacteria at a concentration of 64 g/mL. A further *Penicillium steckii* strain was obtained from saline environment of mangrove plant *Avicennia marina* and evaluated for antifungal activity in potato dextrose agar against dieback pathogen of rose [Sabat and Gupta, African Journal of Microbiology Research Vol. 4 (3), pp. 126-135, 4 February, 2010].

Although it is well known in the technical field of controlling phytopathogenic fungi to apply biopesticides, such as bacteria or fungi which are not detrimental to the plant or crop to be treated, there is a need for further biopesticides.

SUMMARY OF THE INVENTION

Said need is met by the provision of a novel fungal strain of the genus *Penicillium* isolated from a soil sample. This fungus was shown to be effective in controlling harmful fungi such as *Alternaria solani*, *Botrytis cinerea* and *Phytophthora infestans* on tomatoes, and culture medium of this fungus showed inhibitory activity against the conidial germination of the rice blast fungus *Magnaporthe oryzae*, the major fungal threat to cultivated rice. Bioactivity guided fractionation of organic extracts led to the isolation of novel tanzawaic acids, the structures of which were elucidated by 2D-NMR spectroscopy as well as mass spectrometry.

The present invention thus relates to *Penicillium* strains, which are selected from the group consisting of:
a. strain IBWF104-06 as deposited with DSMZ under the deposit number DSM 27859; and
b. strains having at least one identifying characteristic of said strain IBWF104-06.

The present invention further relates to cell-free extracts of the strains of the invention and to culture media obtainable by culturing the strains of the invention in a culture medium and separating the medium from the culture broth.

The present invention further relates to the tanzawaic acids of formula (1), (2), (3) and (4):

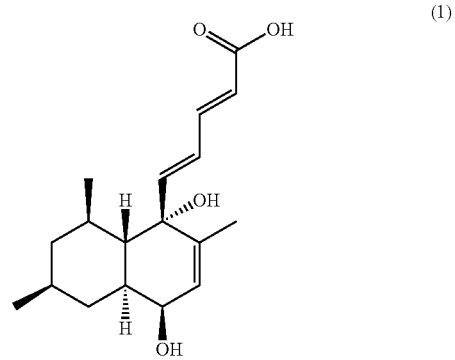

(1)

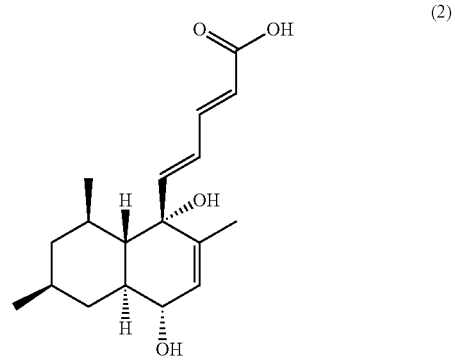

(2)

-continued

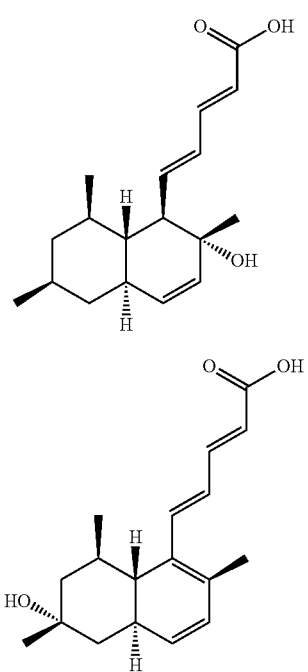

(3)

(4)

and the agriculturally acceptable salts thereof, and to methods of preparing the tanzawaic acids of the invention which method comprises culturing the strains of the invention and isolating said tanzawaic acids from the culture broth.

The present invention further relates to compositions comprising the strains, cell-free extracts, culture media, and tanzawaic acids and salts of the invention, respectively, as well as to their use for controlling or suppressing plant pathogens or preventing plant pathogen infection, and to corresponding methods which comprise treating the pathogens, their habitat or the materials or plants to be protected against pathogen attack, or the soil or propagation material with an effective amount of the strains, cell-free extracts, culture media, tanzawaic acids and salts, and compositions of the invention, respectively.

Further embodiments of the invention are disclosed in the claims and figures and in the following detailed description of the invention.

BRIEF DESCRIPTION OF THE DRAWINGS

FIG. 1 shows the ITS sequence of *Penicillium steckii* strain IBWF104-06 (SEQ ID NO:1).

DETAILED DESCRIPTION OF THE INVENTION

The invention relates to strain IBWF104-06. This strain was deposited under the Budapest treaty with DSMZ on Oct. 9, 2013 and has been assigned deposit number DSM 27859.

Strain IBWF104-06 was determined to belong to the genus *Penicillium* based on morphological observations which are consistent with strain IBWF104-06 being a *Penicillium steckii* strain (see Houbraken, et al., Fungal Diversity (2010) 44: 117-133). This is confirmed by its ITS sequence which has a high degree of identity with other *Penicillium steckii* strains, such as *Penicillium steckii* strain CBS 122389, *Penicillium steckii* strain CBS 122388 and *Penicillium steckii* strain CBS 122390. The Internal Transcribed Spacer (ITS) refers to a piece of non-functional RNA situated between structural ribosomal RNAs (rRNA) on a common precursor transcript and sequence comparison of the ITS region is widely used in taxonomy and molecular phylogeny for elucidating relationships among congeneric species and closely related genera.

Strain IBWF104-06 was further determined to have potent antifungal activity. In particular, it was found to be effective against infestation with plant pathogens including *Phytophthora infestans*, *Botrytis cinerea* and *Alternaria solani*.

Strain IBWF104-06 was further determined to produce certain extrolites.

The term "extrolite" refers to secondary metabolites produced by a microorganism (such as fungi and bacteria, in particular the strains of the invention) that has pesticidal activity or improves plant growth, water use efficiency of the plant, plant health, plant appearance, or the population of beneficial microorganisms in the soil around the plant activity.

Extrolites produced by strain IBWF104-06 include the following tanzawaic acids of formula (1), (2), (3), and (4):

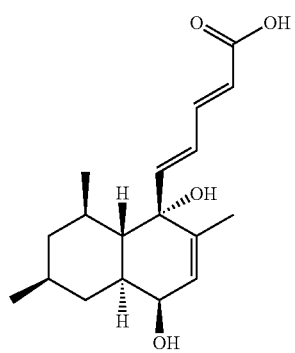

(1)

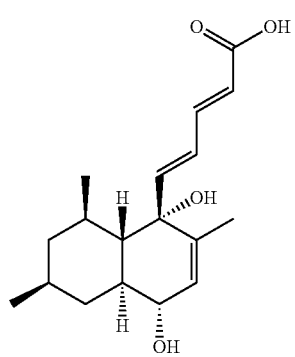

(2)

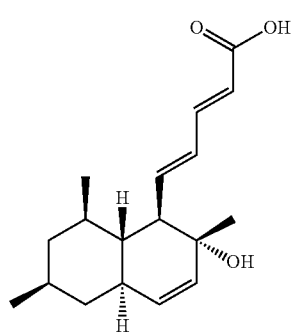

(3)

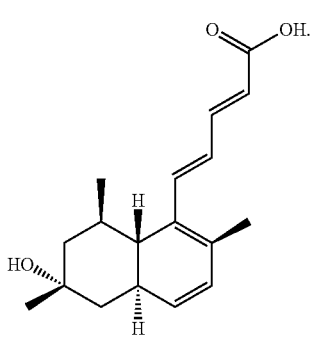

(4)

Extrolites produced by strain IBWF104-06 further include arohynapene A, arohynapene B, tanzawaic acid A, and tanzawaic acid E.

In addition to strain IBWF104-06, the invention relates to any *Penicillium* strain, whether physically derived from the original deposit of strain IBWF104-06 or independently isolated, so long as they retain at least one of the identifying characteristics of the deposited *Penicillium* strain IBWF104-06. Such *Penicillium* strains of the invention include any progeny of strain IBWF104-06, including mutants of said strain.

Mutant strains of *Penicillium* strain IBWF104-06 may be obtained by methods well-known in the art. For example, such mutants are attainable by applying a mutagenic chemical agent, such as N-methyl-nitrosoguanidine, X-ray or UV radiation. Subsequent to said treatment a screening for mutant strains showing the desired characteristics may be performed. Thus, the term mutant is meant to designate a *Penicillium* strain obtained by direct mutant selection but also includes *Penicillium* strains that have been further mutagenized or otherwise manipulated (e.g., via the introduction of a plasmid). Accordingly, embodiments include both naturally occurring and artificially induced mutants.

In particular, the *Penicillium* strains of the invention are characterized in that they are capable of retaining at least one of the identifying characteristics, when cultivated between about 20 and about 27° C. in:

YMG medium (4 g/l yeast extract, 10 g/l malt extract, 10 g/l glucose, pH 5.5) and/or YM medium (4 g/l yeast extract, 10 g/l malt extract, 4 g/l glucose, pH 5.5) and/or DM medium (40 g/l malt extract, pH 5.5) and/or PDA medium (24 g/l Difco Potato Dextrose Broth).

The *Penicillium* strains of the invention are preferably capable of retaining at least one of the identifying characteristics, when cultivated between about 20 and about 27° C. in all of the said media.

The strains of the invention are in particular *Penicillium steckii* strains.

According to one aspect, a *Penicillium steckii* strain of the invention is one whose ITS sequence has at least 95%, preferably at least 98% and in particular at least 99% nucleotide sequence identity with the ITS sequence of strain IBWF104-06, i.e. SEQ ID NO:1.

According to a further aspect, a *Penicillium steckii* strain of the invention is one having the following morphological characteristics:

No growth on CYA at 37° C., reverse colours on CYA in shades of créme (créme, pale créme, yellow-créme or brown créme), and broadly ellipsoidal conidia, optionally in combination with one or more (in particular all) of the following morphological characteristics:

Colony diameter, 7 days, in mm: CYA 24-32; MEA 21-30; YES 29-40;

Moderate or good sporulation on CYA with grey green conidia, soluble pigments absent, reverse in shades of créme;

Moderate to good sporulation on YES, grey or dull green conidia, reverse light yellow, soluble pigment absent;

Colonies on MEA grey green or dull green;

No reaction with Ehrlich test;

Conidiophores from surface hyphae, symmetrically biverticillate;

Metulae 13-18×2.1-3.3 μm;

Phialides ampulliform, 7-10×2.0-3.0 μm;

Conidia smooth walled, broadly ellipsoidal, 2.0-3.1×2.0-2.6 μm.

"Identity" between two nucleotide sequences means identity of the residues over the complete length of the aligned sequences, such as, for example, the identity calculated (for rather similar sequences) with the aid of the program Bio-Edit Version 7.2.2 (Hall, T. A. 1999. BioEdit: a user-friendly biological sequence alignment editor and analysis program for Windows 95/98/NT. Nucl. Acids. Symp. Ser. 41:95-98.) using default parameters for "pairwise alignment (optimal GLOBAL alignment)".

An identifying characteristic of the deposited *Penicillium* strain IBWF104-06 is that it is capapble of producing at least one of the following tanzawaic acids:

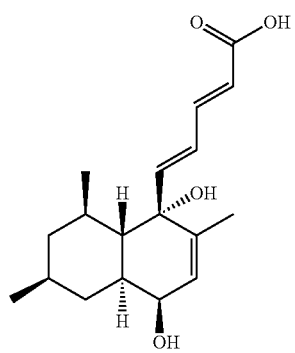

(1)

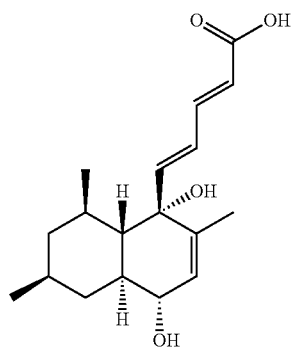

(2)

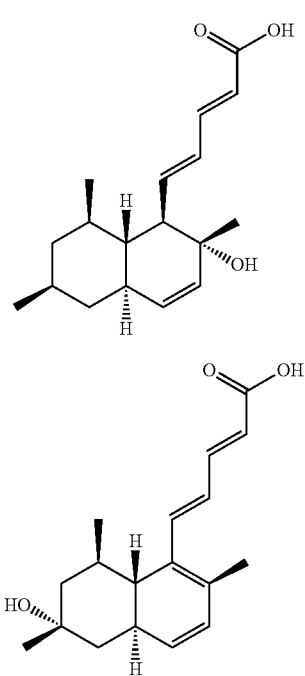

or an agriculturally acceptable salt thereof.

Thus, according to one aspect of the invention, *Penicillium* strains of the invention are capable of producing one or more of said tanzawaic acids, preferably at least tanzawaic acid of formula (3) or tanzawaic acid of formula (4), more preferably at least both of tanzawaic acid of formula (3) and tanzawaic acid of formula (4), and particularly all four tanzawaic acids, or the respective salts thereof.

In particular, the *Penicillium* strains of the invention are characterized in that they are capable of producing the said tanzawaic acid(s) when cultivated between about 20 and about 27° C. in:

YMG medium (4 g/l yeast extract, 10 g/l malt extract, 10 g/l glucose, pH 5.5) and/or
YM medium (4 g/l yeast extract, 10 g/l malt extract, 4 g/l glucose, pH 5.5) and/or
DM medium (40 g/l malt extract, pH 5.5) and/or
PDA medium (24 g/l Difco Potato Dextrose Broth).

The *Penicillium* strains of the invention are preferably capable of producing the said tanzawaic acid(s) between about 20 and about 27° C. in all of the said media.

A further identifying characteristic of the deposited *Penicillium* strain IBWF104-06 is that is capable of producing at least one compound selected from the group consisting of arohynapene A, arohynapene B, tanzawaic acid A and tanzawaic acid E in addition to its capability of producing one or more of the tanzawaic acids of formula (1), (2), (3) and (4).

Thus, according to a further aspect of the invention, *Penicillium* strains of the invention are capable of producing one or more of the tanzawaic acids of formula (1), (2), (3) and (4), or the respective salts thereof as disclosed herein, and of producing at least one compound selected from the group consisting of arohynapene A, arohynapene B, tanzawaic acid A and tanzawaic acid E.

A further identifying characteristic of the deposited *Penicillium* strain IBWF104-06 is its antifungal activity. In particular, it was found to be effective against infestion with plant pathogens including *Phytophthora infestans*, *Botrytis cinerea* and *Alternaria solani*. It is further effective against infestion with *Fusarium graminearum*.

Thus, according to a further aspect of the invention, *Penicillium* strains of the invention have antifungal activity, particularly against a plant pathogen selected from the group consisting of *Phytophthora infestans*, *Botrytis cinerea* and *Alternaria solani*. More particularly, *Penicillium* strains of the invention have antifungal activity against at least two or against all of said pathogens. The *Penicilium* strains of the invention may alternatively or additionally have antifungal activity against *Fusarium graminearum*.

Antifungal activity of the *Penicillium* strains against plant pathogens can be determined in an in-vitro confrontation assay using the desired plant pathogen, in particular a phytopathogenic fungus such as *Phytophthora infestans*, *Botrytis cinerea* or *Alternaria solani* as follows:

The plant pathogen, in particular the phytopathogenic fungus, is grown on ISP2 medium comprising per litre: 10 g malt extract (Sigma Aldrich, 70167); 4 g Bacto yeast extract (Becton Dickinson, 212750); 4 g glucose monohydrate (Sigma Aldrich, 16301); 20 g Agar (Becton Dickinson, 214510), pH about 7, Aq. bidest. Alternatively, V8 medium is used comprising per litre: 200 mL of vegetable juice, 3 g calcium carbonate (Merck Millipore, 1020660250); 30 g Agar (Becton Dickinson, 214510), pH 6.8, Aq. bidest. ISP2 medium is particularly useful if the phytopathogenic fungus is *Botrytis cinerea* or *Alternaria solani*. V8 medium is particularly useful if the phytopathogenic fungus is *Phytophthora infestans*.

The *Penicillium* strains are point-inoculated on one side of an agar plate. An agar block (approx. 0.3 cm$^2$) containing one actively growing fungal plant pathogen is put in the center of the plate. After incubating for 7-14 days at about 25° C., the growth of the plant pathogen is examined, especially for inhibition zones. According to the invention, a *Penicillium* strain has antifungal activity if there is one or more of the following: (i) antibiosis (determined by evaluating the diameter of the pathogen-free zone (zone of inhibition)); (ii) competition (determined by comparing the diameter of the growth of the fungal pathogen on plates with the strain in comparison to control plates) and/or (iii) mycoparasitism (dertermined by the microscopical observation that the strain over-grows the fungal pathogen and mycoparasites the pathogen).

More specifically, the present invention relates to the deposited strain IBWF104-06 and any *Penicillium* strain having one or more of the identifying characteristics of the deposited strain, wherein the identifying characteristics are selected from the group consisting of:

(a) an antifungal activity against a plant pathogen selected from the group consisting of *Phytophthora infestans*, *Botrytis cinerea* and *Alternaria solani*, as disclosed herein;

(b) the capability of producing at least one compound selected from the group consisting of tanzawaic acid of formula (1), (2), (3) and (4), or the respective salts thereof, as disclosed herein; and (c) the capability of producing at least one compound selected from the group consisting of arohynapene A, arohynapene B, tanzawaic acid A and tanzawaic acid E, as disclosed herein.

In particular, *Penicillium* strains of the invention have two or more of the identifying characteristics of the deposited strain, with strains having at least the characteristics (a) and (b) being particularly preferred. For instance, according to a preferred embodiment, the strains of the invention (a) have an antifungal activity against a plant pathogen selected from the group consisting of *Phytophthora infestans, Botrytis cinerea* and *Alternaria solani* and (b) are capable of producing at least tanzawaic acid of formula (3) or tanzawaic acid of formula (4), more preferably at least both of tanzawaic acid of formula (3) and tanzawaic acid of formula (4), and particularly all of tanzawaic acids of formula (1), (2), (3) and (4). According to a further preferred embodiment, the strains of the invention (a) have an antifungal activity against two or against all of the plant pathogens selected from the group consisting of *Phytophthora infestans, Botrytis cinerea* and *Alternaria solani* and (b) are capable of producing at least one compound selected from the group consisting of tanzawaic acid of formula (1), (2), (3) and (4), or the respective salts thereof. In another instance, the strains of the invention show antifungal activity against *Fusarium graminearum* in addition to the said identifying characteristics.

According to an embodiment of the invention, the strains of the invention are provided in isolated or substantially purified form.

The terms "isolated" or "substantially purified" are meant to denote that the strains of the invention have been removed from a natural environment and have been isolated or separated, and are at least 60% free, preferably at least 75% free, and more preferably at least 90% free, even more preferably at least 95% free, and most preferably at least 100% free from other components with which they were naturally associated. An isolate obtained by culturing a single microbial colony is an example of an isolated strain of the invention.

The strains of the invention may be provided in any physiological state such as active or dormant. Dormant strains may be provided for example frozen, dried, or lyophilized or partly desiccated (procedures to produce partly desiccated organisms are given in WO 2008/002371) or in form of spores.

According to an embodiment of the invention, the strains of the invention are provided in the form of spores, e.g. in the form of condiospores.

Conidiospores (also called conidia) are asexual spores that are generated through mitosis.

According to a further embodiment of the invention, the strains of the invention are provided as a whole broth culture comprising a strain of the invention. "Whole broth culture" refers to a liquid culture containing both cells and media. A whole broth culture may comprise the strains in a growth medium without any additional additives or materials or in combination with suitable nutrient mixtures.

The culture is preferably an isolated or substantially purified culture.

An "isolated culture" or "substantially purified culture" refers to a culture of the strains of the invention that does not include significant amounts of other materials which normally are found in natural habitat in which the strain grows and/or from which the strain normally may be obtained. Such an "isolated culture" or "substantially purified culture" does normally not include any other microorganism in quantities sufficient to interfere with the replication of the strain of the invention. Isolated cultures of the invention may, however, be combined to prepare a mixed culture of the strains of the invention and a further microbial biopesticide.

The strains of the invention can be cultivated continuously or discontinuously in the batch process or in the fed batch or repeated fed batch process. A review of known methods of cultivation will be found in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)). The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981). These culture media that can be used according to the invention generally comprise one or more sources of carbon, sources of nitrogen, inorganic salts, vitamins and/or trace elements. Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid. Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soybean protein, yeast extract, meat extract and others. The sources of nitrogen can be used separately or as a mixture. Inorganic salt compounds that may be present in the media comprise the chloride, phosphate or sulfate salts of calcium, magnesium, sodium, cobalt, molybdenum, potassium, manganese, zinc, copper and iron. Inorganic sulfur-containing compounds, for example sulfates, sulfites, dithionites, tetrathionates, thiosulfates, sulfides, but also organic sulfur compounds, such as mercaptans and thiols, can be used as sources of sulfur. Phosphoric acid, potassium dihydrogenphosphate or dipotassium hydrogenphosphate or the corresponding sodium-containing salts can be used as sources of phosphorus. Chelating agents can be added to the medium, in order to keep the metal ions in solution. Especially suitable chelating agents comprise dihydroxyphenols, such as catechol or protocatechuate, or organic acids, such as citric acid. The culture media used may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growing media can also be obtained from commercial suppliers, such as Standard 1 (Merck) or BHI (Brain heart infusion, DIFCO) etc. All components of the medium are sterilized, either by heating (20 min at 2.0 bar and 121° C.) or by sterile filtration. The components can be sterilized either together, or if necessary separately. All the components of the medium can be present at the start of growing, or optionally can be added continuously or by batch feed. The temperature of the culture of the respective microorganism is normally between 20° C. and 35° C., preferably 20° C. to 30° C. and can be kept constant or can be varied during the experiment. The pH value of the medium should be in the range from 5 to 7, preferably around 5.5. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 35° C. Culture is continued until a maximum of the desired product has formed. This is normally achieved within 11 days to 13 days.

In particular, the strains of the invention may be cultivated on 2% malt solid media for 3-4 days at 20 to 30° C. In liquid culture, condiospores can be produced. In large liquid cultures, aeration may be necessary. The fungal cells (vegative cells and spores) can be washed and concentrated (e.g. by centrifugation at room temperature for about 15 min at 7000×g).

The invention also relates to culture medium obtainable by culturing the strains of the invention in a culture medium and separating medium from the culture broth, e.g., the supernatant of a whole broth culture, i.e., the liquid broth remaining when cells grown in broth are removed by centrifugation, filtration, sedimentation, or other means well known in the art.

Such culture medium contains pesticidal extrolites which are produced by the cultured strain.

The invention also relates to cell-free extracts of the strains of the invention.

The term "cell-free extract" refers to an extract of the vegetative cells, spores and/or the whole culture broth of a strain of the invention, which is obtainable by cell disruption methods known in the art such as solvent-based methods (e.g. organic solvents such as alcohols sometimes in combination with suitable salts), temperature-based methods, application of shear forces, cell disruption with an ultrasonicator, high-frequency ultrasound, by high pressure, e.g. in a French pressure cell, by osmolysis, by the action of detergents, lytic enzymes, by means of homogenizers or by a combination of several of the methods listed. The desired extract may be concentrated by conventional concentration techniques such as drying, evaporation, centrifugation or alike. Certain washing steps using organic solents and/or water-based media may also be applied to the crude extract preferably prior to use.

Such extract contains pesticidal extrolites which are produced by the cultured strain.

Fungicidal extrolites that are specific to the strains of the invention may be recovered from such medium or extract according to conventional methods in particular when the strains of the invention have been cultivated on YMG medium (yeast extract 4.0 g/L, malt extract 10 g/L, glucose 10 g/L, with the pH value being adjusted to 5.5 before autoclaving). The same methods can be applied to strains of the invention that have been cultivated on HA medium, DM medium, PDA medium or the like.

Conventional isolation or purification methodology known in the art includes, but is not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like. For example the agent can be recovered from culture media by first removing the microorganisms. The remaining broth is then passed through or over a cation exchange resin to remove unwanted cations and then through or over an anion exchange resin to remove unwanted inorganic anions and organic acids.

The pesticidal extrolites from the strains of the invention are in particular selected from the tanzawaic acids of formula (1), (2), (3) and (4), which can be extracted and isolated from cultures of the strains of the invention. Moreover, said tanzawaic acids may be synthesized, as tanzawaic acid A is synthetically available [Arimoto, et al., Tetrahedron Letters 39 (1998) 9513-9516].

The invention also relates to the agriculturally acceptable salts, particularly base addition salts of said tanzawaic acids. Said salts can be obtained by conventional methods well known in the art, e.g. by reacting the compounds of the invention with a suitable base to form a base addition salt, or with a suitable alcohol or amine to form an ester or amide.

Suitable cations to form the salts of the invention are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

The invention further relates to agrochemical compositions comprising an auxiliary and at least one or more of the strains, cell-free extracts, culture media and extrolites, of the invention, respectively.

The strains, cell-free extracts, culture media, extrolites, and compositions of the invention, respectively, are suitable as antifungal agents or fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The strains, cell-free extracts, culture media, extrolites, and compositions of the invention, respectively, are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, the strains, cell-free extracts culture media, extrolites; and compositions of the invention, respectively, are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the strains, cell-free extracts culture media, extrolites; and compositions of the invention, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The strains, cell-free extracts, culture media, extrolites, and compositions of the invention, respectively, are particularly suitable for controlling the following plant diseases: *Albugo* spp. (white rust) on ornamentals, vegetables (e. g. *A. candida*) and sunflowers (e. g. *A. tragopogonis*); *Altemaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. altemata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*)or Northern leaf blight (*B. zeicola*) on corn, e. g. spot blotch (*B. sorokiniana*) on cereals and e.g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. sofina* or *C. kikuchii*) and rice; *Cladosporium* spp. on tomatoes (e. g. *C. fulvum:* leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus,* anamorph: *B. sorokiniana*) and rice (e. g. *C. miyabeanus,* anamorph: *H. oryzae*); *Colletotrichum* (teleomorph: *Glomerella*) spp. (anthracnose) on cotton (e. g. *C. gossypil*), corn (e. g. *C. graminicola:* Anthracnose stalk rot), soft fruits, potatoes (e. g. *C. coccodes:* black dot), beans (e. g. *C. lindemuthianum*) and soybeans (e. g. *C. truncatum* or *C. gloeosporioides*); *Corticium* spp., e. g. *C. sasakil* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri,* teleomorph: *Neonectria liriodendri:* Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium,* teleomorph: *Pyrenophora*) spp. on corn, cereals, such as barley (e. g. *D. teres,* net blotch) and wheat (e. g. *D. tritici-repentis* tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophllum* and/or *Botlyosphaeria obtusa; Elsinoe* spp. on pome fruits (*E. pyrl*), soft fruits (*E. veneta:* anthracnose) and vines (*E. ampelina:* anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata,* syn. *Libertella blepharis*) on fruit trees, vines and ornamental woods; *Exserohllum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. *glycines* now syn. *F. virguliforme*) and *F. tucumaniae* and

*F. brasillense* each causing sudden death syndrome on soybeans, and *F. vertcillioides* on corn; *Gaeumannomyces graminis* (take-all) on cereals (e. g. wheat or barley) and corn; *Gibberella* spp. on cereals (e. g. *G. zeae*) and rice (e. g. *G. fujikuror:* Bakanae disease); *Glomerella cingulata* on vines, pome fruits and other plants and *G. gossypii* on cotton; Grain staining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera,* teleomorph: *Cochlobolus*) on corn, cereals and rice; *Hemileia* spp., e. g. *H. vastatrix* (coffee leaf rust) on coffee; *Isaropsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici,* Septoria blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata:* stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola:* can and leaf spot) and soybeans (e. g. stem rot: *P. phaseoli,* teleomorph: *Diaporthe phaseoloru*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma,* syn. *P. sojae*), potatoes and tomatoes (e. g. *P. Infestans:* late blight) and broad-leaved trees (e. g. *P. ramorum:* sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e. g. *P. triticina* (brown or leaf rust), *P. striiforms* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *triticirepentis* (tan spot) on wheat or *P. teres* (net blotch) on barley; *Pyriculana* spp., e. g. *P. oryzae* (teleomorph: *Magnaporthe grisea,* rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. coll-cygni* (Ramularia leaf spots, Physio-logical leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secais* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (Septoria blotch) on wheat and *S.* (syn. *Stagonospora*) *nodorum* (*Stagonospora* blotch) on cereals; *Uncinula* (syn. *Erysiphe*) *necator*(powdery mildew, anamorph: *Oidium tuckeri*) on vines; *Setospaeria* spp. (leaf blight) on corn (e. g. *S. turcicum,* syn. *Helminthosporium turcicum*) and turf; *Sphacelotheca* spp. (smut) on corn, (e. g. *S. reiliana:* head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries,* wheat bunt) and *T. controversa* (dwarf bunt) on wheat; *Typhula incamata* (grey snow mold) on barley or wheat; *Urocystis* spp., e. g. *U. occulta* (stem smut) on rye; *Uromyces* spp. (rust) on vegetables, such as beans (e. g. *U. appendiculatus,* syn. *U. phaseoli*) and sugar beets (e. g. *U. betae*); *Ustilago* spp. (loose smut) on cereals (e. g. *U. nuda* and *U. avaenae*), corn (e. g. *U. maydis* corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The strains, cell-free extracts, culture media, extrolites, and compositions of the invention, respectively, are also suitable for controlling harmful fungi in the protection of stored products or harvest and in the protection of materials.

The term "protection of materials" is to be understood to denote the protection of technical and non-living materials, such as adhesives, glues, wood, paper and paper-board, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Scierophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae.*

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The strains, cell-free extracts, culture media, extrolites, and compositions of the invention, respectively, may be used for improving the health of a plant. The invention also relates to a method for improving plant health by treating a plant, its propagation material and/or the locus where the plant is growing or is to grow with an effective amount of the strains, cell-free extracts, culture media, extrolites, and compositions.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The strains, cell-free extracts, culture media, extrolites, and compositions of the invention, respectively, are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

The term "effective amount" denotes an amount which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the tanzawaic acid or salt used.

Plant propagation materials may be treated with the strains, cell-free extracts, culture media, extrolites, and compositions of the invention, respectively, prophylactically either at or before planting or transplanting.

The strains of the invention can be formulated as an inoculant for a plant. The term "inoculant" means a composition that includes an isolated strain of the invention and optionally a carrier, which may include a biologically acceptable medium.

Such inoculants and other suitable compositions can be prepared as compositions comprising besides the active ingredients at least one auxiliary (inert ingredient) by usual means (see e.g. H. D. Burges: Formulation of Micobial Biopesticides, Springer, 1998). Suitable customary types of such compositions are suspensions, dusts, powders, pastes, granules, pressings, capsules, and mixtures thereof. Examples for composition types are suspensions (e.g. SC, OD, FS), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). Herein, it has to be taken into account that each formulation type or choice of auxiliary should not influence the viability of the microorganism during storage of the composition and when finally applied to the soil, plant or plant propagation material. Suitable formulations are e.g. mentioned in WO 2008/002371, U.S. Pat. No. 6,955,912, U.S. Pat. No. 5,422,107.

Examples for suitable auxiliaries are those mentioned herein, wherein it must be taken care that choice and amounts of such auxiliaries should not influence the viability of the microbial pesticides in the composition. Especially for bactericides and solvents, compatibility with the respective microorganism of the respective microbial pesticide has to be taken into account. In addition, compositions with microbial pesticides may further contain stabilizers or nutrients and UV protectants. Suitable stabilzers or nutrients are e.g. alpha-tocopherol, trehalose, glutamate, potassium sorbate, various sugars like glucose, sucrose, lactose and maltodextrine (H. D. Burges: Formulation of Micobial Biopesticides, Springer, 1998). Suitable UV protectants are e.g. inorganic compouns like titan dioxide, zinc oxide and iron oxide pigments or organic compounds like benzophenones, benzotriazoles and phenyltriazines. The compositions optionally comprise 0.1-80% stabilizers or nutrients and 0.1-10% UV protectants, in addition to auxiliaries mentioned herein for compositions comprising cell-free extracts, culture media and extrolites.

To produce a dry formulation, fungal cells, preferably spores can be suspended in a suitable dry carrier (e.g. clay). To produce a liquid formulation, cells, preferably spores, can be re-suspended in a suitable liquid carrier (e.g. water-based) to the desired spore density. The spore density number of spores per mL can be determined by identifying the number of colony-forming units (CFU) on agar medium e.g. potato dextrose agar after incubation for several days at room temperature ° C.

When the strains of the invention are employed in crop protection, the application rates preferably range from about $1 \times 10^6$ to $5 \times 10^{15}$ (or more) CFU/ha. Preferably, the spore concentration is about $1 \times 10^7$ to about $1 \times 10^{11}$ CFU/ha.

When the strains of the invention are employed in seed treatment, the application rates with respect to plant propagation material preferably range from about $1 \times 10^6$ to $1 \times 10^{12}$ (or more) CFU/seed. Preferably, the concentration is about $1 \times 10^6$ to about $1 \times 10^{11}$ CFU/seed. Alternatively, the application rates with respect to plant propagation material preferably range from about $1 \times 10^7$ to $1 \times 10^{14}$ (or more) CFU per 100 kg of seed, preferably from $1 \times 10^9$ to about $1 \times 10^{11}$ CFU per 100 kg of seed.

The cell-free extracts, culture media and extrolites of the invention can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of cell-free extract, culture medium or extrolite on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates. Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and in particular between 0.5 and 75%, by weight of active substance. The active substances are employed in a purity of from 90% to 100%, pref-erably from 95% to 100% (according to NMR spectrum).

Examples for composition types and their preparation are:
i) Water-soluble Concentrates (SL, LS)

10-60 wt % of a cell-free extract, culture medium or extrolite of the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a cell-free extract, culture medium or extrolite of the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a cell-free extract, culture medium or extrolite of the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a cell-free extract, culture medium or extrolite of the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a cell-free extract, culture medium or extrolite of the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinyl-alcohol) is added.

vi) Water-dispersible Granules and Water-soluble Granules (WG, SG)

50-80 wt % of a cell-free extract, culture medium or extrolite of the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible Powders and Water-soluble Powders (WP, SP, WS)

50-80 wt % of a cell-free extract, culture medium or extrolite of the invention are ground in a rotor-stator mill with addition of 1-5 wt % dispersants (e.g. sodium ligno-sulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a cell-free extract, culture medium or extrolite of the invention are comminuted with addition of 3-10 wt % dispersants (e.g. sodium ligno-sulfonate), 1-5 wt % thickener (e.g. carboxymethylcellulose) and water ad 100 wt % to give a fine suspension of the active substance. Dilution with water gives a stable suspension of the active substance.

ix) Microemulsion (ME)

5-20 wt % of a cell-free extract, culture medium or extrolite of the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a cell-free extract, culture medium or extrolite of the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a cell-free extract, culture medium or extrolite of the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a cell-free extract, culture medium or extrolite of the invention are ground finely and mixed intimately with solid carrier (e.g. finely divided kaolin) ad 100 wt %.

xii) Granules (GR, FG)

0.5-30 wt % of a cell-free extract, culture medium or extrolite of the invention are ground finely and associated with solid carrier (e.g. silicate) ad 100 wt %. Granulation is achieved by extrusion, spray-drying or fluidized bed.

xiii) Ultra-low Volume Liquids (UL)

1-50 wt % of a cell-free extract, culture medium or extrolite of the invention are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds.

Preferred examples of seed treatment formulation types or soil application for pre-mix compositions are of WS, LS, ES, FS, WG or CS-type.

Typically, a pre-mix formulation for seed treatment application comprises 0.5 to 99.9 percent, especially 1 to 95 percent, of the desired ingredients, and 99.5 to 0.1 percent, especially 99 to 5 percent, of a solid or liquid adjuvant (including, for example, a solvent such as water), where the auxiliaries can be a surfactant in an amount of 0 to 50 percent, especially 0.5 to 40 percent, based on the pre-mix formulation. Whereas commercial products will preferably be formulated as concentrates (e.g., pre-mix composition (formulation)), the end user will normally employ dilute formulations (e.g., tank mix composition).

Seed treatment methods for applying or treating the strains, cell-free extracts, culture media, extrolites and compositions of the invention, respectively, to plant propagation material, especially seeds, are known in the art, and include dressing, coating, filmcoating, pelleting and soaking application methods of the propagation material. Such methods are also applicable to the combinations according to the invention. In a preferred embodiment, the strains, cell-free extracts, culture media, extrolites, and compositions of the invention, respectively, are applied or treated onto the plant propagation material by a method such that the germination is not negatively impacted. Accordingly, examples of suitable methods for applying (or treating) a plant propagation material, such as a seed, is seed dressing, seed coating or seed pelleting and alike.

It is preferred that the plant propagation material is a seed, seed piece (i.e. stalk) or seed bulb.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the ingredients in the strains, cell-free extracts, culture media, extrolites, and compositions of the invention, respectively, and adherence thereof to the seeds is desired during propagation material treatment. Treatment could vary from a thin film (dressing) of the formulation containing the combination, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognizable.

An aspect of the present invention includes application of the strains, cell-free extracts, culture media, extrolites and compositions of the invention, respectively, onto the plant propagation material in a targeted fashion, including positioning the ingredients in the combination onto the entire plant propagation material or on only parts thereof, including on only a single side or a portion of a single side. One of ordinary skill in the art would understand these application methods from the description provided in EP954213B1 and WO06/112700.

The strains, cell-free extracts, culture media, extrolites and compositions of the invention, respectively, can also be used in form of a "pill" or "pellet" or a suitable substrate and placing, or sowing, the treated pill, or substrate, next to a plant propagation material. Such techniques are known in the art, particularly in EP1124414, WO07/67042, and WO07/67044. Application of the strains, cell-free extracts, culture media, extrolites and compositions, respectively, described herein onto plant propagation material also includes protecting the plant propagation material treated with the combination of the present invention by placing one or more pesticide-containing particles next to a pesticide-treated seed, wherein the amount of pesticide is such that the pesticide-treated seed and the pesticide-containing particles together contain an Effective Dose of the pesticide and the pesticide dose contained in the pesticide-treated seed is less than or equal to the Maximal Non-Phytotoxic Dose of the pesticide. Such techniques are known in the art, particularly in WO2005/120226.

Application of the strains, cell-free extracts, culture media, extrolites and compositions of the invention, respectively, onto the seed also includes controlled release coatings on the seeds, wherein the ingredients of the combinations are incorporated into materials that release the ingredients over time. Examples of controlled release seed treatment technologies are generally known in the art and include polymer films, waxes, or other seed coatings, wherein the ingredients may be incorporated into the controlled release material or applied between layers of materials, or both.

Seed can be treated by applying thereto the compound s present in the inventive mixtures in any desired sequence or simultaneously.

The seed treatment occurs to an unsown seed, and the term "unsown seed" is meant to include seed at any period between the harvest of the seed and the sowing of the seed in the ground for the purpose of germination and growth of the plant. Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the strains, cell-free extracts, culture media, extrolites and compositions of the invention, respectively. In particular, seed coating or seed pelleting are preferred. As a result of the treatment, the ingredients are adhered on to the seed and therefore available for pest control.

The treated seeds can be stored, handled, sowed and tilled in the same manner as any other active ingredient treated seed.

In particular, the present invention relates to a method for protection of plant propagation material from pests and/or improving the health of plants grown from said plant propagation material, wherein the soil, wherein plant propagation material is sown, is treated with an effective amount of a strain, cell-free extract, culture medium, extrolite or composition of the invention, respectively.

In particular, the present invention relates to a method for protection of plant propagation material from pests, wherein the soil, wherein plant propagation material is sown, is treated with an effective amount of a strain, cell-free extract, culture medium, extrolite or composition of the invention, respectively.

In particular, the present invention relates to a method for protection of plant propagation material from harmful fungi, wherein the soil, wherein plant propagation material is sown, is treated with an effective amount of a strain, cell-free extract, culture medium, extrolite or composition of the invention, respectively.

In particular, the present invention relates to a method for protection of plant propagation material from animal pests (insects, acarids or nematodes), wherein the soil, wherein plant propagation material is sown, is treated with an effective amount of a strain, cell-free extract, culture medium, extrolite or composition of the invention, respectively.

The user applies the compositions of the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

When it comes to the treatment of plant propagation material, especially seeds, the compositions disclosed herein give, after two-to-tenfold dilution, active substance concentrations of from 0.01 to 60% by weight, preferably from 0.1 to 40%, in the ready-to-use preparations. Application can be carried out before or during sowing. Methods for applying a strain, cell-free extract, culture medium, extrolite or composition of the invention, respectively, onto plant propagation material, especially seeds, include dressing, coating, pelleting, dusting, soaking and in-furrow application methods of the propagation material. Preferably, the strains, cell-free extracts, culture media, extrolites or compositions of the invention, respectively, are applied onto the plant propagation material by a method such that germination is not induced, e. g. by seed dressing, pelleting, coating and dusting.

According to one embodiment, individual components of the composition of the invention such as parts of a kit or parts of a binary or ternary mixture may be mixed by the user himself in a spray tank or any other kind of vessel used for applications (e.g seed treater drums, seed pelleting machinery, knapsack sprayer) and further auxiliaries may be added, if appropriate.

If living microorganisms, such as the strains of the invention, form part of such kit, it must be taken care that choice and amounts of the components (e.g. chemcial pesticidal agents) and of the further auxiliaries should not influence the viability of the microorganisms in the composition mixed by the user. Especially for bactericides and solvents, compatibility with the respective microorganisms has to be taken into account.

Various types of oils, wetters, adjuvants, fertilizer, or micronutrients, and further pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as a virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term pesticides includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology to increase plant growth, biomass, yield or any other quality parameter of the harvestable goods of acrop plant.

Biopesticides are typically created by growing and concentrating naturally occurring organisms and/or their metabolites including bacteria and other microbes, fungi, viruses, nematodes, proteins, etc. They are often considered to be important components of integrated pest management (IPM) programmes.

Biopesticides fall into two major classes, microbial and biochemical pesticides:
(1) Microbial pesticides consist of bacteria, fungi or viruses (and often include the metabolites that bacteria and fungi produce). Entomopathogenic nematodes are also classed as microbial pesticides, even though they are multi-cellular.
(2) Biochemical pesticides are naturally occurring substances that control pests or provide other crop protection uses as defined below, but are relatively non-toxic to mammals.

Mixing the strains, cell-free extracts, culture media, extrolites and compositions of the invention, respectively, in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II (e.g. pesticidally-active substances and biopesticides), in conjunction with which the strains, cell-free extracts, culture media, and extrolites of the invention, respectively, can be used, is intended to illustrate the possible combinations but does not limit them:
A) Respiration Inhibitors
Inhibitors of complex III at $Q_o$ site (e.g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17) and 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21);
inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl] amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4- methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1 H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-tri-methyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e.g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S, 3R)-3-(2-chlorophenyl)-2-(2,4-difluorophenyl)-oxiranylmethyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)-phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)-phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluoro-phenypisoxazol-4-yl]-(3-pyridyl) methanol (B.1.50);

Delta14-reductase inhibitors: aldimorph (B.2.1), dodemorph (B.2.2), dodemorphacetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofosmethyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-

(4-cyano-phenyl)ethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e.g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadinetri-acetate (H.4.7), iminoctadine-tris(albesilate) (H.4.8), dithianon (H.4.9), 2,6-di-methyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino)-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-meth-oxy-pyridin-3-yl) cyclopropanecarboxylic acid amide (K.1.38), 5-chloro-1-(4,6-di-methoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-y0-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phenyl]propan-2-ol (K.1.44), 3-(5-fluoro-3,3,4,4-tetramethyl-3,4-dihydroisoquinolin-1-yl)-quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47);

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea f. catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum;* mixture of *T. harzianum* and *T. viride;* mixture of *T. polysporum* and *T. harzianum; T. stromaticum, T. virens* (also named *Gliocladium virens*), *T. viride, Typhula phacorrhiza, Ulocladium oudemansii, Verticillium dahlia,* zucchini yellow mosaic virus (avirulent strain);

L2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;

L3) Microbial pesticides with insecticidal, acaricidal, molluscidal and/or nematicidal activity: *Agrobacterium radiobacter, Bacillus cereus, B. firmus, B. thuringien-* sis, *B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* sp., *Chromobacterium subtsugae, Cydia pomonella granulosis* virus, *Cryptophlebia leucotreta granulovirus* (CrleGV), *Isaria fumosorosea, Heterorhabditis bacteriophora, Lecanicillium longisporum, L. muscarium* (formerly *Verticillium lecanii*), *Metarhizium anisopliae, M. anisopliae* var. *acridum, Nomuraea rileyi, Paecilomyces fumosoroseus, P. lilacinus, Paenibacillus popilliae, Pasteuria* spp., *P. nishizawae, P. penetrans, P. ramose, P. reneformis, P. thornea, P. usgae, Pseudomonas fluorescens, Steinernema carpocapsae, S. feltiae, S. kraussei;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, *Acacia negra* extract, extract of grapefruit seeds and pulp, extract of *Chenopodium ambrosiodae*, Catnip oil, Neem oil, Quillay extract, Tagetes oil;

L5) Microbial pesticides with plant stress reducing, plant growth regulator, plant growth promoting and/or yield enhancing activity: *Azospirillum amazonense A. brasilense, A. lipoferum, A. irakense, A. halopraeferens, Bradyrhizobium* sp., *B. elkanii, B. japonicum, B. liaoningense, B. lupini, Delftia acidovorans, Glomus intraradices, Mesorhizobium* sp., *Paenibacillus alvei, Penicillium bilaiae, Rhizobium leguminosarum* bv. *phaseolii, R. l. trifolii, R. l.* bv. *viciae, R. tropici, Sinorhizobium meliloti;*

L6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinlide, humates, jasmonic acid or salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract;

M) Growth Regulators abscisic acid (M.1.1), amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;

amino acid derivatives: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;

cyclohexanediones: butroxydim, clethodim (N.6.1), cycloxydim (N.6.2), profoxydim (N.6.3), sethoxydim (N.6.4), tepraloxydim (N.6.5), tralkoxydim;

dinitroanilines: benfluralin, ethalfluralin, oryzalin, pendimethalin (N.7.1), prodiamine (N.7.2), trifluralin (N.7.3);

diphenyl ethers: acifluorfen (N.8.1), aclonifen, bifenox, diclofop, ethoxyfen, fomesafen, lactofen, oxyfluorfen;

hydroxybenzonitriles: bomoxynil (N.9.1), dichlobenil, ioxynil;

imidazolinones: imazamethabenz, imazamox (N.10.1), imazapic (N.10.2), imazapyr (N.10.3), imazaquin (N.10.4), imazethapyr (N.10.5);

phenoxy acetic acids: clomeprop, 2,4-dichlorophenoxyacetic acid (2,4-D) (N.11.1), 2,4-DB, dichlorprop, MCPA, MCPA-thioethyl, MCPB, Mecoprop;

pyrazines: chloridazon (N.11.1), flufenpyr-ethyl, fluthiacet, norflurazon, pyridate;

pyridines: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuronmethyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam;

ureas: chlorotoluron, daimuron, diuron (N.15.1), fluometuron, isoproturon, linuron, methabenzthiazuron, tebuthiuron;

other acetolactate synthase inhibitors: bispyribac-sodium, cloransulam-methyl, diclosulam, florasulam (N.16.1), flucarbazone, flumetsulam, metosulam, orthosulfamuron, penoxsulam, propoxycarbazone, pyribambenzpropyl, pyribenzoxim, pyriftalid, pyriminobac-methyl, pyrimisulfan, pyrithiobac, pyroxasulfone (N.16.2), pyroxsulam;

others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidonethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O.1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids: allethrin (O.3.1), bifenthrin (O.3.2), cyfluthrin (O.3.3), cyhalothrin (O.3.4), cyphenothrin (O.3.5), cypermethrin (O.3.6), alpha-cypermethrin (O.3.7), beta-cypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), taufluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);

insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7);

macrocyclic lactone insecticides: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) I acaricides: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflumizone (O.14.2);

ryanodine receptor inhibitors: chlorantraniliprole (O.15.1), cyantraniliprole (O.15.2), flubendiamide (O.15.3), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.15.4); N-[4-chloro-2-[(diethyl-lambda-4-sulfanylidene)carbannoyl]-6-methyl-phenyl]-2-(3-chloro-2-pyridyl)-5-(trifluoromethyl)pyrazole-3-carboxamide (O.15.5); N-[4-chloro-2-[(di-2-propyl-lambda-4-sulfanylidene)carbannoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfanylidene)carbannoyl]-phenyl]-2-(3-chloro-2-pyridyl)-5-(trifluoromethyl)pyrazole-3-carboxamide (O.15.7); N-[4,6-dichloro-2-[(diethyl-lambda-4-sulfanylidene)carbannoyl]-phenyl]-2-(3-chloro-2-pyridyl)-5-(difluoromethyl)pyrazole-3-carboxamide (O.15.8); N-[4,6-dibromo-2-[di-2-propyl-lambda-4-sulfanylidene)carbamoyl]-phenyl]-2-(3-chloro-2-pyridyl)-5-(trifluoromethyl)pyrazole-3-carboxamide (O.15.9); N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide (O.15.11);

others: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15) and 1,1'-[(3S,4R,4aR,6S,6aS,12R,12aS,12bS)-4-[[(2-cyclopropylacetyl)-oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]cyclopropaneacetic acid ester (O.16.16).

The present invention furthermore relates to agrochemical compositions comprising a mixture of at least one strain, cell-free extract, culture medium or extrolite of the invention (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of the strains, cell-free extracts, culture media or extrolites of the invention and at least one fungicide from groups A) to L), as described above, is more efficient than combating those fungi with individual strains, cell-free extracts, culture media or extrolites of the invention or individual fungicides from groups A) to L). By applying the strains, cell-free extracts, culture media or extrolites of the invention together with at least one active substance from groups A) to O) a synergistic effect can be obtained, i.e. more then simple addition of the individual effects is obtained (synergistic mixtures).

This can be obtained by applying the strains, cell-free extracts, culture media or extrolites of the invention and at least one further active substance simultaneously, either jointly (e. g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

When applying the strains, cell-free extracts, culture media or extrolites of the invention and a pesticide II sequentially the time between both applications may vary e.g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In case of a mixture comprising a pesticide II selected from group L), it is preferred that the pesticide II is applied as last treatment.

According to the invention, the solid material (dry matter) of the biopesticides (with the exception of oils such as Neem oil, Tagetes oil, etc.) are considered as active components (e.g. to be obtained after drying or evaporation of the extraction medium or the suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1 \times 10^9$ CFU equals one gram of total weight of the respective active component. Colony forming unit is measure of viable microbial cells, in particular fungal and bacterial cells. In addition, here " CFU" may also be understood as the number of (juvenile) individual nematodes in case of (entomopathogenic) nematode biopesticides, such as *Steinernema feltiae*.

In the binary mixtures and compositions according to the invention the weight ratio of the component 1) and the component 2) generally depends from the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiments of the binary mixtures and compositions, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiments of the binary mixtures and compositions, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for mixtures applied by seed treatment.

Preference is also given to mixtures comprising as component 2) at least one active substance selected from group A), which is particularly selected from (A.1.1), (A.1.4), (A.1.8), (A.1.9), (A.1.12), (A.1.13), (A.1.14), (A.1.17), (A.1.19), (A.1.21), (A.2.1), (A.2.2), (A.3.2), (A.3.3), (A.3.4), (A.3.7), (A.3.8), (A.3.9), (A.3.12), (A.3.14), (A.3.15), (A.3.16), (A.3.19), (A.3.20), (A.3.21), (A.3.22), (A.3.23), (A.3.24), (A.3.25), (A.3.26), (A.3.27); (A.4.5), (A.4.6), (A.4.8), (A.4.9) and (A.4.11).

Preference is given to mixtures as component 2) at least one active substance selected from group B), which is particularly selected from (B.1.4), (B.1.5), diniconazole (B.1.6), (B.1.8), (B.1.10), (B.1.11), (B.1.12), (B.1.17), (B.1.18), (B.1.21), (B.1.22), (B.1.23), (B.1.25), (B.1.26), (B.1.27), (B.1.28), (B.1.29), uni (B.1.31), (B.1.32), (B.1.33), (B.1.34), (B.1.35), (B.1.36), (B.1.37), (B.1.38), (B.1.39), (B.1.40), (B.1.41), (B.1.42), (B.1.44), (B.1.46), (B.1.49) and (B.1.50; (B.2.2), (B.2.4), (B.2.5), (B.2.6), piperalin (B.2.7), (B.2.8); and (B.3.1).

Preference is given to mixtures comprising as component 2) at least one active substance selected from group C), which is particularly selected from (C.1.4), C.1.5), (C.1.6), and (C.2.4).

Preference is given to mixtures comprising as component 2) at least one active substance selected from group D), which is particularly selected from (D1.1), (D1.2), (D1.4), (D1.5); (D2.2), (D2.4), (D2.5), (D2.6) and (D2.7);

Preference is also given to mixtures comprising as component 2) at least one active substance selected from group E), which is particularly selected from (E.1.1), (E.1.2), and (E.1.3);

Preference is also given to mixtures comprising as component 2) at least one active substance selected from group F), which is particularly selected from (F.1.2), (F.1.4), (F.1.5), (F.1.6) and (F.2.1).

Preference is also given to mixtures as component 2) at least one active substance selected from group G), which is particularly selected from (G.3.1), (G.3.2), (G.3.3), (G.3.4), (G.3.5), (G.3.6), (G.4.1) and (G.5.1).

Preference is also given to mixtures comprising as component 2) at least one active substance selected from group H), which is particularly selected from (H.1.2), (H.1.3), copper oxychloride (H.1.4), (H.1.5), (H.1.6); (H.2.2), (H.2.5), (H.2.7), (H.3.2), (H.3.3), (H.3.4), (H.3.5), (H.3.6), (H.3.12); (H.4.2), (H.4.6), dithianon (H.4.9) and (H.4.10).

Preference is also given to mixtures comprising as component 2) at least one active substance selected from group I), which is particularly selected from (I.2.3) and (I.2.5).

Preference is also given to mixtures comprising as component 2) at least one active substance selected from group J), which is particularly selected from (J.1.1), (J.1.2), (J.1.3), (J.1.4), (J.1.6), (J.1.7), (J.1.8) and (J.1.9).

Preference is also given to mixtures comprising as component 2) at least one active substance selected from group K), which is particularly selected from (K.1.4), (K.1.5), (K.1.8), (K.1.12), (K.1.14), (K.1.15), (K.1.19) and (K.1.22).

The biopesticides from group L) of pesticides II, their preparation and their pesticidal activity e.g. against harmful fungi or insects are known (e-Pesticide Manual V 5.2 (ISBN 978 1 901396 85 0) (2008-2011).

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) and/or L6) may also have fungicidal, bactericidal, viricidal, plant defense activator, insecticidal, acaricidal, molluscidal, pheromone and/or nematicidal activity.

Many of these biopesticides are registered and/or are commercially available: aluminium silicate (Screen™ Duo from Certis LLC, USA), *Agrobacterium radiobacter* K1026 (e.g. NoGall® from Becker Underwood Pty Ltd., Australia), *A. radiobacter* K84 (Nature 280, 697-699, 1979; e.g. Gall-Troll® from AG Biochem, Inc., C, USA), *Ampelomyces quisqualis* M-10 (e.g. AQ 10® from Intrachem Bio GmbH & Co. KG, Germany), *Ascophyllum nodosum* (Norwegian kelp, Brown kelp) extract or filtrate (e.g. ORKA GOLD from Becker Underwood, South Africa; or Goemar® from Laboratoires Goemar, France), *Aspergillus flavus* NRRL 21882 isolated from a peanut in Georgia in 1991 by the USDA, National Peanut Research Laboratory (e.g. in Afla-Guard® from Syngenta, CH), mixtures of *Aureobasidium pullulans* DSM14940 and DSM 14941 (e.g. blastospores in Blossom-Protect® from bio-ferm GmbH, Germany), *Azospirillum brasilense* XOH (e.g. AZOS from Xtreme Gardening, USA or RTI Reforestation Technologies International; USA), *Bacillus amyloliquefaciens* FZB42 (e.g. in RhizoVital® 42 from AbiTEP GmbH, Berlin, Germany), *B. amyloliquefaciens* IN937a (J. Microbiol. Biotechnol. 17(2), 280-286, 2007; e.g. in BioYield® from Gustafson LLC, TX, USA), *B. amyloliquefaciens* IT-45 (CNCM 1-3800) (e.g. Rhizocell C from ITHEC, France), *B. amyloliquefaciens* subsp. *plantarum* MB1600 (NRRL B-50595, deposited at United States Department of Agriculture) (e.g. Integral®, Subtilex® NG from Becker Underwood, USA), *B. cereus* CNCM 1-1562 (U.S. Pat. No. 6,406,690), *B. firmus* CNCM 1-1582 (WO 2009/126473, WO 2009/124707, U.S. Pat. No. 6,406,690; Votivo® from Bayer Crop Science LP, USA), *B. pumilus* GB34 (ATCC 700814; e.g. in YieldShield® from Gustafson LLC, TX, USA), and *Bacillus pumilus* KFP9F (NRRL B-50754) (e.g. in BAC-UP or FUSION-P from Becker Underwood South Africa), *B. pumilus* QST 2808 (NRRL B-30087) (e.g. Sonata® and Ballad® Plus from AgraQuest Inc., USA), *B. subtilis* GB03 (e.g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B-21661 in Rhapsody®, Serenade® MAX and Serenade® ASO from AgraQuest Inc., USA), *B. subtilis* var. *amyloliquefaciens* FZB24 (e.g. Taegro® from Novozyme Biologicals, Inc., USA), *B. subtilis* var. *amyloliquefaciens* D747 (e.g. Double Nickel 55 from Certis LLC, USA), *B. thuringiensis* ssp. *aizawai* ABTS-1857 (e.g. in XenTari® from BioFa AG, Münsingen, Germany), *B. t.* ssp. *aizawai* SAN 401 I, ABG-6305 and ABG-6346, *Bacillus t.* ssp. *israelensis* AM65-52 (e.g. in VectoBac® from Valent BioSciences, IL, USA), *Bacillus thuringiensis* ssp. *kurstaki* SB4 (NRRL B-50753; e.g. Beta Pro® from Becker Underwood, South Africa), *B. t.* ssp. *kurstaki* ABTS-351 identical to HD-1 (ATCC SD-1275; e.g. in Dipel® DF from Valent BioSciences, IL, USA), *B. t.* ssp. *kurstaki* EG 2348 (e.g. in Lepinox® or Rapax® from CBC (Europe) S.r.l., Italy), *B. t.* ssp. *tenebrionis* DSM 2803 (EP 0 585 215 B1; identical to NRRL B-15939; Mycogen Corp.), *B. t.* ssp. *tenebrionis* NB-125 (DSM 5526; EP 0 585 215 B1; also referred to as SAN 418 1 or ABG-6479; former production strain of Novo-Nordisk), *B. t.* ssp. *tenebrionis* NB-176 (or NB-176-1) a gamma-irridated, induced high-yielding mutant of strain NB-125 (DSM 5480; EP 585 215 B1; Novodor® from Valent BioSciences, Switzerland), *Beauveria bassiana* ATCC 74040 (e.g. in Naturalis® from CBC (Europe) S.r.I., Italy), *B. bassiana* DSM 12256 (US 200020031495; e.g. BioExpert® SC from Live Sytems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e.g. BroadBand® from Becker Underwood, South Africa), *B. brongniartii* (e.g. in Melocont® from Agrifutur, Agrianello, Italy, for control of cockchafer; J. Appl. Microbiol. 100(5),1063-72, 2006), *Bradyrhizobium* sp. (e.g. Vault® from Becker Underwood, USA), *B. japonicum* (e.g. VAULT® from Becker Underwood, USA), *Candida oleophila* I-182 (NRRL Y-18846; e.g. Aspire® from Ecogen Inc., USA, Phytoparasitica 23(3), 231-234, 1995), *C. oleophila* strain O (NRRL Y-2317; Biological Control 51, 403-408, 2009), *Candida*

*saitoana* (e.g. Biocure® (in mixture with lysozyme) and BioCoat® from Micro Flo Company, USA (BASF SE) and Arysta), Chitosan (e.g. Armour-Zen® from BotriZen Ltd., NZ), *Clonostachys rosea* f. *catenulata*, also named *Gliocladium catenulatum* (e.g. isolate J 1446: Prestop® from Verdera Oy, Finland), *Chromobacterium subtsugae* PRAA4-1 isolated from soil under an eastern hemlock (*Tsuga canadensis*) in the Catoctin Mountain region of central Maryland (e.g. in GRANDEVO from Marrone Bio Innovations, USA), *Coniothyrium minitans* CON/M/91-08 (e.g. Contans® WG from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Cryptophlebia leucotreta* granulovirus (CrleGV) (e.g. in CRYPTEX from Adermatt Biocontrol, Switzerland), *Cydia pomonella* granulovirus (CpGV) V03 (DSM GV-0006; e.g. in MADEX Max from Andermatt Biocontrol, Switzerland), CpGV V22 (DSM GV-0014; e.g. in MADEX Twin from Adermatt Biocontrol, Switzerland), *Delftia acidovorans* RAY209 (ATCC PTA-4249; WO 2003/57861; e.g. in BIOBOOST from Brett Young, Winnipeg, Canada), *Dilophosphora alopecuri* (Twist Fungus from Becker Underwood, Australia), *Ecklonia maxima* (kelp) extract (e.g. KELPAK SL from Kelp Products Ltd, South Africa), formononetin (e.g. in MYCONATE from Plant Health Care plc, U.K.), *Fusarium oxysporum* (e.g. BIO-FOX® from S.I.A.P.A., Italy, FUSACLEAN® from Natural Plant Protection, France), *Glomus intraradices* (e.g. MYC 4000 from ITHEC, France), *Glomus intraradices* RTI-801 (e.g. MYKOS from Xtreme Gardening, USA or RTI Reforestation Technologies International; USA), grapefruit seeds and pulp extract (e.g. BC-1000 from Chemie S.A., Chile), harpin (alpha-beta) protein (e.g. MESSENGER or HARP-N-Tek from Plant Health Care plc, U.K.; Science 257, 1-132, 1992), *Heterorhabditis bacteriophaga* (e.g. Nemasys® G from Becker Underwood Ltd., UK), *Isaria fumosorosea* Apopka-97 (ATCC 20874) (PFR-97™ from Certis LLC, USA), cis-jasmone (U.S. Pat. No. 8,221,736), laminarin (e.g. in VACCIPLANT from Laboratoires Goemar, St. Malo, France or Stähler SA, Switzerland), *Lecanicillium longisporum* KV42 and KV71 (e.g. VERTALEC® from Koppert BV, Netherlands), *L. muscarium* KV01 (formerly *Verticillium lecanii*) (e.g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from *Ornithacris cavroisi* in Niger; also NRRL 50758) (e.g. GREEN MUSCLE® from Becker Underwood, South Africa), *M. a.* var. *acridum* FI-985 (e.g. GREEN GUARD® SC from Becker Underwood Pty Ltd, Australia), *M. anisopliae* FI-1045 (e.g. BIOCANE® from Becker Underwood Pty Ltd, Australia), *M. anisopliae* F52 (DSM 3884, ATCC 90448; e.g. MET52® Novozymes Biologicals BioAg Group, Canada), *M. anisopliae* ICIPE 69 (e.g. METATHRIPOL from ICIPE, Nairobe, Kenya), *Metschnikowia fructicola* (NRRL Y-30752; e.g. SHEMER® from Agrogreen, Israel, now distributed by Bayer CropSciences, Germany; U.S. Pat. No. 6,994,849), *Microdochium dimerum* (e.g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e.g. in development products Muscudor™ or QRD300 from AgraQuest, USA), Neem oil (e.g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e.g. NO FLY™ from Natural Industries, Inc., USA), *P. lilacinus* 251 (e.g. in BioAct®/MeloCon® from Prophyta, Germany; Crop Protection 27, 352-361, 2008; originally isolated from infected nematode eggs in the Philippines), *P. lilacinus* DSM 15169 (e.g. NEMATA® SC from Live Systems Technology S.A., Colombia), *P. lilacinus* BCP2 (NRRL 50756; e.g. PL GOLD from Becker Underwood BioAg SA Ltd, South Africa), mixture of *Paenibacillus alvei* NAS6G6 (NRRL B-50755), *Pantoea vagans* (formerly agglomerans) C9-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* spp. ATCC PTA-9643 (WO 2010/085795), *Pasteuria* spp. ATCC SD-5832 (WO 2012/064527), *P. nishizawae* (WO 2010/80169), *P. penetrans* (US 5,248,500), *P. ramose* (WO 2010/80619), *P. thornea* (WO 2010/80169), *P. usgae* (WO 2010/80169), *Penicillium bilaiae* (e.g. Jump Start® from Novozymes Biologicals BioAg Group, Canada, originally isolated from soil in southern Alberta; Fertilizer Res. 39, 97-103, 1994), *Phlebiopsis gigantea* (e.g. RotStop® from Verdera Oy, Finland), *Pichia anomala* WRL-076 (NRRL Y-30842; U.S. Pat. No. 8,206,972), potassium bicarbonate (e.g. Amicarb® fromm Stähler SA, Switzerland), potassium silicate (e.g. Sil-MATRIX™ from Certis LLC, USA), *Pseudozyma flocculosa* PF-A22 UL (e.g. Sporodex® from Plant Products Co. Ltd., Canada), *Pseudomonas* sp. DSM 13134 (WO 2001/40441, e.g. in PRORADIX from Sourcon Padena GmbH & Co. KG, Hechinger Str. 262, 72072 Tubingen, Germany), *P. chloraphis* MA 342 (e.g. in CERALL or CEDEMON from BioAgri AB, Uppsala, Sweden), *P. fluorescens* CL 145A (e.g. in ZEQUANOX from Marrone BioInnovations, Davis, Calif., USA; J. Invertebr. Pathol. 113(1):104-14, 2013), *Pythium oligandrum* DV 74 (ATCC 38472; e.g. POLYVERSUM® from Remeslo SSRO, Biopreparaty, Czech Rep. and GOWAN, USA; US 2013/0035230), *Reynoutria sachlinensis* extract (e.g. REGALIA® SC from Marrone BioInnovations, Davis, Calif., USA), *Rhizobium leguminosarum* bv. *phaseolii* (e.g. RHIZO-STICK from Becker Underwood, USA), *R. l. trifolii* RP113-7 (e.g. DORMAL from Becker Underwood, USA; Appl. Environ. Microbiol. 44(5), 1096-1101), *R. l.* bv. *viciae* P1NP3Cst (also referred to as 1435; New Phytol 179(1), 224-235, 2008; e.g. in NODULATOR PL Peat Granule from Becker Underwood, USA; or in NODULATOR XL PL bfrom Becker Underwood, Canada), *R. l.* bv. *viciae* SU303 (e.g. NODULAID Group E from Becker Underwood, Australia), *R. l.* bv. *viciae* WSM1455 (e.g. NODULAID Group F from Becker Underwood, Australia), *R. tropici* SEMIA 4080 (identical to PRF 81; Soil Biology & Biochemistry 39, 867-876, 2007), *Sinorhizobium meliloti* MSDJ0848 (INRA, France) also referred to as strain 2011 or RCR2011 (Mol Gen Genomics (2004) 272: 1-17; e.g. DORMAL ALFALFA from Becker Underwood, USA; NITRAGIN® Gold from Novozymes Biologicals BioAg Group, Canada), *Sphaerodes mycoparasitica* IDAC 301008-01 (WO 2011/022809), *Steinernema carpocapsae* (e.g. MILLENIUM® from Becker Underwood Ltd., UK), *S. feltiae* (NEMASHIELD® from BioWorks, Inc., USA; NEMASYS® from Becker Underwood Ltd., UK), *S. kraussei* L137 (NEMASYS® L from Becker Underwood Ltd., UK), *Streptomyces griseoviridis* K61 (e.g. MYCOSTOP® from Verdera Oy, Espoo, Finland; Crop Protection 25, 468-475, 2006), *S. lydicus* WYEC 108 (e.g. Actinovate® from Natural Industries, Inc., USA, U.S. Pat. No. 5,403,584), *S. violaceusniger* YCED-9 (e.g. DT-9® from Natural Industries, Inc., USA, U.S. Pat. No. 5,968,503), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. asperellum* ICC 012 (e.g. in TENET WP, REMDIER WP, BIOTEN WP from Isagro N.C., USA, BIO-TAM from AgraQuest, USA), *T. atroviride* LC52 (e.g. SENTINEL® from Agrimm Technologies Ltd, NZ), *T. atroviride* CNCM I-1237 (e.g. in Esquive WG from Agrauxine S.A., France, e.g. against pruning wound diseases on vine and plant root pathogens), *T. fertile* JM41 R (NRRL 50759; e.g. RICHPLUS™ from Becker Underwood Bio Ag SA Ltd, South Africa), *T. gamsii* ICC 080 (e.g. in TENET WP, REMDIER WP, BIOTEN WP from Isagro N.C., USA, BIO-TAM from AgraQuest, USA), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), T. virens GL-21 (also named *Gliocladium virens*) (e.g. SOIL-GARD® from Certis LLC, USA), T. viride (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy) and *Ulocladium oudemansii* HRU3 (e.g. in BOTRY-ZEN® from Botry-Zen Ltd, NZ).

Strains can be sourced from genetic resource and deposition centers: American Type Culture Collection, 10801 University Blvd., Manassas, VA 20110-2209, USA (strains with ATCC prefic); CABI Europe - International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-Institut DSMZ-Deutsche Sammlung von Mikroorganismen und Zellkulturen GmbH, Inhoffenstraβe 7 B, 38124 Braunschweig, Germany (strains with prefix DSM); International Depositary Authority of Canada Collection, Canada (strains with prefix IDAC); Interntional Collection of Micro-orgniasms from Plants, Landcare Research, Private Bag 92170, Auckland Mail Centre, Auckland 1142, New Zealand (strans with prefix ICMP); IITA, PMB 5320, Ibadan, Nigeria (straisn with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Illinois 61604 USA (strains with prefix NRRL); Department of Scientific and Industrial Research Culture Collection, Applied Biochemistry Division, Palmerston North, New Zealand (strains with prefix NZP); FEPAGRO-Fundação Estadual de Pesquisa Agropecuária, Rua Gonçalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Room 19-9, Beltsville, MD 20705, USA (strains with prefix USDA: Beltsville Rhizobium Culture Collection Catalog March 1987 USDA-ARS ARS-30; and Murdoch University, Perth, Western Australia (strains with prefix WSM). Further strains may be found at the Global catalogue of Microorganisms.

*Bacillus amyloliquefaciens* subsp. *plantarum* MBI600 (NRRL B-50595) is deposited under accession number NRRL B-50595 with the strain designation *Bacillus subtilis* 1430 (and identical to NCIMB 1237). Recently, MBI 600 has been re-classified as *Bacillus amyloliquefaciens* subsp. *plantarum* based on polyphasic testing which combines classical microbiological methods relying on a mixture of traditional tools (such as culture-based methods) and molecular tools (such as genotyping and fatty acids analysis). Thus, *Bacillus subtilis* MBI600 (or MBI 600 or MBI-600) is identical to *Bacillus amyloliquefaciens* subsp. *plantarum* MBI600, formerly *Bacillus subtilis* MBI600. *Bacillus amyloliquefaciens* MBI600 is known as plant growth-promoting rice seed treatment from Int. J. Microbiol. Res. 3(2) (2011), 120-130 and further described e.g. in US 2012/0149571 A1. This strain MBI600 is e.g. commercially available as liquid formulation product INTEGRAL® (Becker-Underwood Inc., USA).

*Bacillus subtilis* strain FB17 was originally isolated from red beet roots in North America (System Appl. Microbiol 27 (2004) 372-379). This *B. subtilis* strain promotes plant health (US 2010/0260735 A1; WO 2011/109395 A2). *B. subtilis* FB17 has also been deposited at ATCC under number PTA-11857 on Apr. 26, 2011. *Bacillus subtilis* strain FB17 may be referred elsewhere to as UD1022 or UD10-22.

*Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. japonicum* SEMIA 5079 (e.g. Gelfix 5 or Adhere 60 from Nitral Urbana Laoboratories, Brazil, a BASF Company), *B. japonicum* SEMIA 5080 (e.g. GELFIX 5 or ADHERE 60 from Nitral Urbana Laoboratories, Brazil, a BASF Company), *B. mojavensis* AP-209 (NRRL B-50616), *B. solisalsi* AP-217 (NRRL B-50617), *B. pumilus* strain INR-7 (otherwise referred to as BU-F22 (NRRL B-50153) and BU-F33 (NRRL B-50185)), *B. simplex* ABU 288 (NRRL B-50340) and *B. amyloliquefaciens* subsp. *plantarum* MBI600 (NRRL B-50595) have been mentioned i.a. in US patent appl. 20120149571, U.S. Pat. No. 8,445,255, WO 2012/079073. *Bradyrhizobium japonicum* USDA 3 is known from U.S. Pat. No. 7,262,151.

Jasmonic acid or salts (jasmonates) or derivatives include without limitation potassium jasmonate, sodium jasmonate, lithium jasmonate, ammonium jasmonate, dimethyl-ammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-1-oxo-indane-4-carbonyl)-amino]-3-methyl -pentanoic acid methyl ester), linoleic acid or derivatives thereof and cis-jasmone, or combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

According to one embodiment of the mixtures of the invention, the at least one pesticide II is selected from the groups L1) to L6):

L1) Microbial pesticides with fungicidal, bactericidal, viricidal and/or plant defense activator activity: *Ampelomyces quisqualis* M-10 (L.1.1), *Aspergillus flavus* NRRL 21882 (L1.2), *Aureobasidium pullulans* DSM 14940 (L1.3), *A. pullulans* DSM 14941 (L.1.4), *Bacillus amyloliquefaciens* AP-136 (NRRL B-50614) (L.1.5), *B. amyloliquefaciens* AP-188 (NRRL B-50615) (L.1.6), *B. amyloliquefaciens* AP-218 (NRRL B-50618) (L.1.7), *B. amyloliquefaciens* AP-219 (NRRL B-50619) (L.1.8), *B. amyloliquefaciens* AP-295 (NRRL B-50620) (L.1.9), *B. amyloliquefaciens* FZB42 (L.1.10), *B. amyloliquefaciens* IN937a (L.1.11), *B. amyloliquefaciens* IT-45 (CNCM I-3800) (L.1.12), *B. amyloliquefaciens* subsp. *plantarum* MBI600 (NRRL B-50595) (L.1.13), *B. mojavensis* AP-209 (NRRL B-50616) (L.1.15), *B. pumilus* INR-7 (otherwise referred to as BU-F22 (NRRL B-50153) and BU-F33 (NRRL B-50185)) (L.1.14), *B. pumilus* KFP9F (L.1.15), *B. pumilus* QST 2808 (NRRL B-30087) (L.1.16), *B. pumilus* GHA 181 (L.1.17), *B. simplex* ABU 288 (NRRL B-50340) (L.1.18), *B. solisalsi* AP-217 (NRRL B-50617) (L.1.19), *B. subtilis* CX-9060 (L.1.20), *B. subtilis* GB03 (L.1.21), *B. subtilis* GB07 (L.1.22), *B. subtilis* QST-713 (NRRL B-21661) (L.1.23), *B. subtilis* var. *amyloliquefaciens* FZB24 (L.1.24), *B. subtilis* var. *amyloliquefaciens* D747 (L.1.25), *Candida oleophila* I-82 (L.1.26), *C. oleophila* O (L.1.27), *C. saitoana* (L.1.28), *Clavibacter michiganensis* (bacteriophages) (L.1.29), *Coniothyrium minitans* CON/M/91-08 (L.1.30), *Cryphonectria parasitica* (L.1.31), *Cryptococcus albidus* (L.1.32), *Dilophosphora alopecuri* (L.1.33), *Fusarium oxysporum* (L.1.34), *Clonostachys rosea* f. *catenulata* J1446 (also named *Gliocladium catenulatum*) (L.1.35), *Gliocladium roseum* 321U (L.1.36), *Metschnikowia fructicola* NRRL Y-30752 (L.1.37), *Microdochium dimerum* (L.1.38), *Microsphaeropsis ochracea* P130A (L.1.39), *Muscodor albus* QST 20799 (L.1.40), *Paenibacillus polymyxa* PKB1 (ATCC 202127) (L.1.41), *Pantoea vagans* C9-1 (L.1.42), *Phlebiopsis gigantea* (L.1.43), *Pichia anomala* WRL-76 (L.1.44), *Pseudozyma flocculosa* PF-A22 UL (L.1.45), *Pythium oligandrum* DV 74 (L.1.46), *Sphaerodes mycoparasitica* IDAC 301008-01 (L.1.47), *Streptomyces griseoviridis* K61 (L.1.48), *S. lydicus* WYEC 108 (L.1.49), *S. violaceusniger* XL-2 (L.1.50), *S. violaceusniger* YCED-9 (L.1.51), *Talaromyces flavus* V117b (L.1.52), *Trichoderma asperellum* T34 (L.1.53), *T. asperellum* SKT-1 (L.1.54), *T. asperellum* ICC 012 (L.1.55), *T. atroviride* LC52 (L.1.56), *T. atroviride* CNCM I-1237 (L.1.57), *T. fertile* JM41R (L.1.58), *T. gamsii* ICC 080 (L.1.59), *T. harmatum* TH 382 (L.1.60), *T. harzianum* TH-35 (L.1.61), *T. harzianum* T-22 (L.1.62), *T. harzianum* T-39 (L.1.63); mixture of *T. harzianum* ICC012 and *T. viride* ICC080 (L.1.64); mixture of *T. polysporum* and *T. harzianum* (L.1.65); *T. stromaticum* (L.1.66), *T. virens* (also named *Gliocladium virens*) GL-21 (L.1.67), *T. virens* G41 (L.1.68), *T. viride* TV1 (L.1.69), *Typhula phacorrhiza* 94671 (L.1.70), *Uloclaudium oudemansii* HRU3 (L.1.71), *Verticillium dahlia* (L.1.72), zucchini yellow mosaic virus (avirulent strain) (L.1.73);

L2) Biochemical pesticides with fungicidal, bactericidal, viricidal and/or plant defense activator activity: chitosan (hydrolysate) (L.2.1), harpin protein (L.2.2), laminarin (L.2.3), Menhaden fish oil (L.2.4), natamycin (L.2.5), Plum pox virus coat protein (L.2.6), potassium bicarbonate (L.2.7), *Reynoutria sachlinensis* extract (L.2.8), salicylic acid (L.2.9), potassium or sodium bicarbonate (L.2.10), tea tree oil (L.2.11);

L3) Microbial pesticides with insecticidal, acaricidal, molluscidal and/or nematicidal activity: *Agrobacterium radiobacter* K1026 (L.3.1), *A radiobacter* K84 (L.3.2), *Bacillus firmus* I-1582 (L.3.3); *B. thuringiensis* ssp. *aizawai* strains ABTS-1857 (L.3.4), SAN 401 I (L.3.5), ABG-6305 (L.3.6) and ABG-6346 (L.3.7); *B. t.* ssp. *israelensis* AM65-52 (L.3.8), *B. t.* ssp. *israelensis* SUM-6218 (L.3.9), *B. t.* ssp. *galleriae* SDS-502 (L.3.10), *B. t.* ssp. *kurstaki* EG 2348 (L.3.11), *B. t.* ssp. *kurstaki* SB4 (L.3.12), *B. t.* ssp. *kurstaki* ABTS-351 (HD-1) (L.3.13), *Beauveria bassiana* ATCC 74040 (L.3.14), *B. bassiana* GHA (L.3.15), *B. bassiana* H123 (L.3.16), *B. bassiana* DSM 12256 (L.3.17), *B. bassiana* PPRI 5339 (L.3.18), *B. brongniartii* (L.3.19), *Burkholderia* sp. A396 (L.3.20), *Chromobacterium subtsugae* PRAA4-1 (L.3.21), *Cydia pomonella granulosis* virus V22 (L.3.22), *Cydia pomonella granulosis* virus V1 (L.3.23), *Isaria fumosorosea* Apopka-97 (L.3.24), *Lecanicillium longisporum* KV42 (L.3.25), *L. longisporum* KV71 (L.3.26), *L. muscarium* (formerly *Verticillium lecanii*) KV01 (L.3.27), *Metarhizium anisopliae* FI-985 (L.3.28), *M. anisopliae* FI-1045 (L.3.29), *M. anisopliae* F52 (L.3.30), *M. anisopliae* ICIPE 69 (L.3.31), *M. anisopliae* var. *acridum* IMI 330189 (L.3.32); *Nomuraea rileyi* strains SA86101 (L.3.33), GU87401 (L.3.34), SR86151 (L.3.35), CG128 (L.3.36) and VA9101 (L.3.37); *Paecilomyces fumosoroseus* FE 9901 (L.3.38), *P. lilacinus* 251 (L.3.39), *P. lilacinus* DSM 15169 (L.3.40), *P. lilacinus* BCP2 (L.3.41), *Paenibacillus popilliae* Dutky-1940 (NRRL B-2309 =ATCC 14706) (L.3.42), *P. popilliae* KLN 3, *P. popilliae* Dutky 1 (L.3.43), *Pasteuria* spp. Ph3 (L.3.44), *Pasteuria* spp. ATCC PTA-9643 (L.3.45), *Pasteuria* spp. ATCC SD-5832 (L.3.46), *P. nishizawae* PN-1 (L.3.46), *P. penetrans* (L.3.47), *P. ramose* (L.3.48), *P. reneformis* Pr-3 (L.3.49), *P. thornea* (L.3.50), *P. usgae* (L.3.51), *Pseudomonas fluorescens* CL 145A (L.3.52), *Steinernema carpocapsae* (L.3.53), *S. feltiae* (L.3.54), *S. kraussei* L137 (L.3.55);

L4) Biochemical pesticides with insecticidal, acaricidal, molluscidal, pheromone and/or nematicidal activity: L-carvone (L.4.1), citral (L.4.2), (E,Z)-7,9-dodecadien-1-yl acetate (L.4.3), ethyl formate (L.4.4), (E,Z)-2,4-ethyl decadienoate (pear ester) (L.4.5), (Z,Z,E)-7,11,13-hexadecatrienal (L.4.6), heptyl butyrate (L.4.7), isopropyl myristate (L.4.8), cis-jasmone (L.4.9), lavanulyl senecioate (L.4.10), 2-methyl 1-butanol (L.4.11), methyl eugenol (L.4.12), methyl jasmonate (L.4.13), (E,Z)-2,13-octadecadien-1-ol (L.4.14), (E,Z)-2,13-octadecadien-1-ol acetate (L.4.15), (E,Z)-3,13-octadecadien-1-ol (L.4.16), R-1-octen-3-ol (L.4.17), penta-termanone (L.4.18), potassium silicate (L.4.19), sorbitol actanoate (L.4.20), (E,Z, Z)-3,8,11-tetradecatrienyl acetate (L.4.21), (Z,E)-9,12-tetradecadien-1-yl acetate (L.4.22), Z-7-tetradecen-2-one (L.4.23), Z-9-tetradecen-1-ylacetate (L.4.24), Z-11-tetradecenal (L.4.25), Z-11-tetradecen-1-ol (L.4.26), *Acacia negra* extract (L.4.27), extract of grapefruit seeds and pulp (L.4.28), extract of *Chenopodium ambrosiodae* (L.4.29), Catnip oil (L.4.30), Neem oil (L.4.31), Quillay extract (L.4.32), Tagetes oil (L.4.33);

L5) Microbial pesticides with plant stress reducing, plant growth regulator, plant growth promoting and/or yield enhancing activity: *Azospirillum amazonense* BR 11140 (SpY2T) (L.5.1), *A. brasilense* AZ39 (L.5.2), *A. brasilense* XOH (L.5.3), *A. brasilense* BR 11005 (Sp245) (L.5.4), *A. brasilense* BR 11002 (L.5.5), *A. lipoferum* BR 11646 (Sp31) (L.5.6), *A. irakense* (L.5.7), *A. halopraeferens* (L.5.8), *Bradyrhizobium* sp. PNL01 (L.5.9), *B.* sp. (*Arachis*) CB1015 (L.5.10), *B.* sp. (*Arachis*) USDA 3446 (L.5.11), *B.* sp. (*Arachis*) SEMIA 6144 (L.5.12), *B.* sp. (*Arachis*) SEMIA 6462 (L.5.13), *B.* sp. (*Arachis*) SEMIA 6464 (L.5.14), *B.* sp. (*Vigna*) (L.5.15), *B. elkanii* SEMIA 587 (L.5.16), *B. elkanii* SEMIA 5019 (L.5.17), *B. elkanii* U-1301 (L.5.18), *B. elkanii* U-1302 (L.5.19), *B. elkanii* USDA 74 (L.5.20), *B. elkanii* USDA 76 (L.5.21), *B. elkanii* USDA 94 (L.5.22), *B. elkanii* USDA 3254 (L.5.23), *B. japonicum* 532c (L.5.24), *B. japonicum* CPAC 15 (L.5.25), *B. japonicum* E-109 (L.5.26), *B. japonicum* G49 (L.5.27), *B. japonicum* TA-11 (L.5.28), *B. japonicum* USDA 3 (L.5.29), *B. japonicum* USDA 31 (L.5.30), *B. japonicum* USDA 76 (L.5.31), *B. japonicum* USDA 110 (L.5.32), *B. japonicum* USDA 121 (L.5.33), *B. japonicum* USDA 123 (L.5.34), *B. japonicum* USDA 136 (L.5.35), *B. japonicum* SEMIA 566 (L.5.36), *B. japonicum* SEMIA 5079 (L.5.37), *B. japonicum* SEMIA 5080 (L.5.38), *B. japonicum* WB74 (L.5.39), *B. liaoningense* (L.5.40), *B. lupini* LL13 (L.5.41), *B. lupini* WU425 (L.5.42), *B. lupini* WSM471 (L.5.43), *B. lupini* WSM4024 (L.5.44), *Glomus intraradices* RTI-801 (L.5.45), *Mesorhizobium* sp. WSM1271 (L.5.46), *M.* sp. WSM1497 (L.5.47), *M. ciceri* CC1192 (L.5.48), *M. huakii* (L.5.49), *M. loti* CC829 (L.5.50), *M. loti* SU343 (L.5.51), *Paenibacillus alvei* NAS6G6 (L.5.52), *Penicillium bilaiae* (L.5.53), *Rhizobium leguminosarum* bv. *phaseolii* (L.5.54), *R. l. trifolii* RP113-7 (L.5.55), *R. l.* bv. *viciae* SU303 (L.5.56), *R. l.* bv. *viciae* WSM1455 (L.5.57), *R. l.* bv. *viciae* P1NP3Cst (L.5.58) *R. tropici* SEMIA 4088 (L.5.59), *Sinorhizobium meliloti* MSDJ0848 (L.5.60);

L6) Biochemical pesticides with plant stress reducing, plant growth regulator and/or plant yield enhancing activity: abscisic acid (L.6.1), aluminium silicate (kaolin) (L.6.2), 3-decen-2-one (L.6.3), formononectin (L.6.4), genistein (L.6.5), hesperetin (L.6.6), homobrassinlide (L.6.7), humates (L.6.8), methyl jasmonate (L.6.9), cis-jasmone (L.6.10), lysophosphatidyl ethanlamine (L.6.11), naringenin (L.6.12), polymeric polyhydroxy acid (L.6.13), salicylic acid (L.6.14), *Ascophyllum nodosum* (Norwegian kelp, Brown kelp) extract (L.6.15) and *Ecklonia maxima* (kelp) extract (L.6.16).

The present invention furthermore relates to agrochemical compositions comprising a mixture of the strains, cell-free extracts, culture media or extrolites of the invention (component 1) and at least one biopesticide selected from the group L) (component 2), in particular at least one further fungicidal biopesticide selected from the groups L1) and L2), as described above, and if desired at least one suitable auxiliary.

Preference is also given to mixtures comprising as pesticide II (component 2) a biopesticide from group L1), preferably selected from *Bacillus amyloliquefaciens* AP-136 (NRRL B-50614 and B-50330), *B. amyloliquefaciens* AP-188 (NRRL B-50615 and B-50331), *B. amyloliquefaciens* AP-218 (NRRL B-50618), *B. amyloliquefaciens* AP-219 (NRRL B-50619 and B-50332), *B. amyloliquefaciens* AP-295 (NRRL B-50620 and B-50333), *B. amyloliquefaciens* IT-45 (CNCM 1-3800), *B. amyloliquefaciens* subsp. *plantarum* MBI600 (NRRL B-50595), *B. mojavensis* AP-209 (NRRL B-50616), *B. pumilus* INR-7 (otherwise referred to as BU-F22 (NRRL B-50153) and BU-F33 (NRRL B-50185)), *B. pumilus* KFP9F, *B. pumilus* QST 2808 (NRRL B-30087), *B. pumilus* GHA 181, *B. simplex* ABU 288 (NRRL B-50340), *B. solisalsi* AP-217 (NRRL B-50617), *B. subtilis* CX-9060, *B. subtilis* GB03, *B. subtilis* GB07, *B. subtilis* QST-713 (NRRL B-21661), *B. subtilis* var. *amyloliquefaciens* FZB24, *B. subtilis* var. *amyloliquefaciens* D747, *Paenibacillus alvei* NAS6G6, *Paenibacillus polymyxa* PKB1 (ATCC 202127), *Sphaerodes mycoparasitica* IDAC 301008-01 and *Trichoderma fertile* JM41R, even more preferably from *Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. amyloliquefaciens* IT-45 (CNCM 1-3800), *B. mojavensis* AP-209 (NRRL B-50616), *B. pumilus* INR-7 (otherwise referred to as BU-F22 (NRRL B-50153) and BU-F33 (NRRL B-50185)), *B. pumilus* QST 2808 (NRRL B-30087), *B. simplex* ABU 288 (NRRL B-50340), *B. subtilis* QST-713 (NRRL B-21661), *B. subtilis* MBI600 (NRRL B-50595), *Paenibacillus alvei* NAS6G6, *Sphaerodes nnycoparasitica* IDAC 301008-01 and *Trichoderma fertile* JM41R.

According to one embodiment of the mixtures of the invention, the at least one pesticide II is *Bacillus amyloliquefaciens* subsp. *plantarum* MBI600. These mixtures are particularly suitable in soybean.

According to another embodiment of the mixtures of the invention, the at least one pesticide II is *B. pumilus* strain INR-7. These mixtures are particularly suitable in soybean and corn.

According to a further embodiment, the at least one pesticide II is *Bacillus simplex,* preferably *B. simplex* strain ABU 288. These mixtures are particularly suitable in soybean and corn.

According to one embodiment of the mixtures of the invention, the at least one pesticide II is selected from *Bacillus amyloliquefaciens* AP-136, *B. amyloliquefaciens* AP-188, *B. amyloliquefaciens* AP-218, *B. amyloliquefaciens* AP-219, *B. amyloliquefaciens* AP-295, *B. amyloliquefaciens* FZB42, *B. amyloliquefaciens* IN937a, *B. amyloliquefaciens* IT-45, *B. amyloliquefaciens* subsp. *plantarum* MBI600, *B. mojavensis* AP-209, *B. pumilus* GB34, *B. pumilus* INR-7, *B. pumilus* KFP9F, *B. pumilus* QST 2808, *B. pumilus* GHA 181, *B. simplex* ABU 288, *B. solisalsi* AP-217, *B. subtilis* CX-9060, *B. subtilis* GB03, *B. subtilis* GB07, *B. subtilis* QST-713, *B. subtilis* var. *amyloliquefaciens* FZB24 and *B. subtilis* var. *amyloliquefaciens* D747. These mixtures are particularly suitable in soybean and corn, in particular for seed treatment.

According to a further embodiment, the at least one pesticide II is selected from *Streptomyces* spp. Preferably from *S. griseoviridis*, *S. lydicus* and *S. violaceusniger*, in particular from strains *S. griseoviridis* K61, *S. lydicus* WYEC 108, *S. violaceusniger* XL-2 and *S. violaceusniger* YCED-9.

According to a further embodiment, the at least one pesticide II is *Sphaerodes mycoparasitica,* preferably *Sphaerodes mycoparasitica* strain IDAC 301008-01 (also referred to as strain SMCD2220-01). These mixtures are particularly suitable in soybean, cereals and corn, in particular corn especially to combat *Fusarium* head blight.

The present invention also relates to mixtures wherein the at least one pesticide II is selected from the following yests and fungi: *Ampelomyces quisqualis,* in particular strain AQ 10, *Aureobasidium pullulans,* in particular blastospores of strain DSM14940 or blastospores of strain DSM 14941 or mixtures thereof; *Candida oleophila,* in particular strains I-182 and O, *Coniothyrium minitans,* in particular strain CON/M/91-8; *Dilophosphora alopecuri* which reduces annual ryegrass toxicity (ARGT), a disease of livestock resulting from the ingestion of annual ryegrass seed-heads that have been infected by the toxin producing bacterium *Rathayibacter toxicus; Gliocladium catenulatum,* in particular strain J 1446; *Metschnikovia fructicola,* in particular strain NRRL Y-30752, *Microsphaeropsis ochracea,* in particular strain P130A for control of apple scab; (2.13) *Muscodor albus,* in particular strain QST 20799, *Pichia anomala,* in particular strain WRL-076, *Pseudozyma flocculosa,* in particular strain PF-A22 UL; *Pythium oligandrum,* in particular strain DV74;

The present invention also relates to mixtures wherein the at least one pesticide II is selected from the fungal genus *Trichoderma,* preferably from the strains *Trichoderma asperellum* T34, *T. asperellum* SKT-1, *T. asperellum* ICC 012, *T. atroviride* LC52, *T. atroviride* CNCM 1-1237, *T. fertile* JM41R, *T. gamsii* ICC 080, *T. harmatum* TH 382, *T. harzianum* TH-35, *T. harzianum* T-22, *T. harzianum* T-39; mixture of *T. harzianum* ICC012 and *T. viride* ICC080; mixture of *T. polysporum* and *T. harzianum; T. stromaticum, T. virens* GL-21, *T. virens* G41 and *T. viride* TV1; in particular *T. fertile* JM41 R.

The present invention also relates to mixtures wherein the at least one pesticide II is selected from the fungal genus *Ulocladium,* in particular *U. oudemansii* HRU3.

Preference is also given to mixtures comprising as pesticide II (component 2) a biopesticide from group L2), preferably selected from chitosan (hydrolysate), methyl-jasmonate, cis-jasmone, laminarin, *Reynoutria sachlinensis* extract and tea tree oil; even more preferable from methyl jasmonate and laminarin.

Preference is also given to mixtures comprising as pesticide II (component 2) a biopesticide from group L3), preferably selected from *Agrobacterium radiobacter* K1026, *Bacillus firmus* I-1582, *Bacillus thuringiensis* ssp. *kurstaki* SB4, *Beauveria bassiana* GHA, *B. bassiana* H123, *B. bassiana* DSM 12256, *B. bassiana* PPRI 5339, *Metarhizium anisopliae* var. *acridum* IMI 330189, *M. anisopliae* FI-985, *M. anisopliae* FI-1045, *M. anisopliae* F52, *M. anisopliae* ICIPE 69, *Paecilomyces lilacinus* DSM 15169, *P. lilacinus* BCP2, *Paenibacillus popilliae* Dutky-1940 (NRRL B-2309=ATCC 14706), *P. popilliae* KLN 3 and *P. popilliae* Dutky 1, even more preferably from *Bacillus thuringiensis* ssp. *kurstaki* SB4, *B. bassiana* DSM 12256, *B. bassiana* PPRI 5339, *Metarhizium anisopliae* var. *acridum* IMI 330189, *M. anisopliae* FI-985, *M. anisopliae* FI-1045, *Paecilomyces lilacinus* DSM 15169, *P. lilacinus* BCP2, *Paenibacillus popilliae* Dutky-1940 (NRRL B-2309=ATCC 14706), *P. popilliae* KLN 3 and *P. popilliae* Dutky 1

According to a further embodiment, the at least one pesticide II is *Beauveria bassiana,* preferably selected from *Beauveria bassiana* ATCC 74040, *B. bassiana* GHA, *B. bassiana* H123, *B. bassiana* DSM 12256 and *B. bassiana* PPRI 5339, in particular *Beauveria bassiana* strain PPRI 5339. These mixtures are particularly suitable for wide range of arthropod pests, such as white flies, thrips, mites, aphids, tingids and all their developmental stages (eggs, immature stages, and adults) infesting numerous crops (vegetables, cucurbits, solanaceous fruits, strawberry, flowers and ornamentals, grapevine, citrus, pome, stone fruits, etc.). Recent studies have shown that these antagonistic fungal strains can effectively control also nut-weevils, wireworms (*Agriotes* spp.), and Tephritid flies, such as the Mediterranean fruit fly, *Ceratitis capitata,* the cherry fruit fly, *Rhagoletis cerasi,* and the olive fly, *Bactrocera oleae.* They are also useful in soybean and corn.

According to a further embodiment, the at least one pesticide II is *Beauveria brongniartii.*

According to a further embodiment, the at least one pesticide II is *Metarhizium anisopliae* or *M. anisopliae* var. *acridium,* preferably selected from *M. anisopliae* FI-1045, *M. anisopliae* F52, *M. anisopliae* var. *acridum* strains FI-985 and IMI 330189, in particular strain IMI 330189. These mixtures are particularly suitable for control of arthropod pests in soybean and corn.

According to a further embodiment, the at least one pesticide II is *Lecanicillium* sp., preferably selected from *Lecanicillium longisporum* KV42, *L. longisporum* KV71 and *L. muscarium* (formerly *Verticillium lecanii*) KV01.

According to a further embodiment, the at least one pesticide II is *Paecilomyces fumosoroseus,* preferably strain FE 9901 especially for white fly control.

According to a further embodiment, the at least one pesticide II is selected from *Nomuraea rileyi,* preferably strains SA86101, GU87401, SR86151, CG128 and VA9101; and *P. lilacinus,* preferably strains 251, DSM 15169 or BCP2, in particular BCP2, which strains especially control the growth of plant-pathogenic nematodes.

According to a further embodiment, the at least one pesticide II is *Bacillus firmus,* preferably spores of strain CNCM I-1582, preferable for seed treatment of soybean and corn against nematodes and insects.

According to a further embodiment, the at least one pesticide II is *B. cereus* preferably spores of CNCM I-1562, preferable for seed treatment of soybean and corn against nematodes and insects.

According to a further embodiment, the at least one pesticide II is a mixture of spores of *B. firmus* and *B. cereus,* preferably mixtures spores of strains CNCM I-1582 and CNCM I-1562, preferable for seed treatment of soybean and corn against nematodes and insects.

According to a further embodiment, the at least one pesticide II is selected from *Bacillus thuringiensis,* preferably *B. thuringiensis* ssp. *aizawai,* in particular *B. t.* ssp. *aizawai* strains ABTS-18, SAN 401 I, ABG-6305 and ABG-6346, which are effective against different lepidopteran species including also noctuidae.

According to a further embodiment, the at least one pesticide II is selected from *Bacillus t.* ssp. *israelensis,* preferably AM65-52, SAN 402 I and ABG-6164, which are applied against larvae of various dipteran pests, e.g. mosquitoes and nematoceres.

According to a further embodiment, the at least one pesticide II is selected from *Bacillus t.* ssp. *kurstaki* preferably from strains EG 2348, SB4 and ABTS-351 (HD-1), in particular *B. thuringiensis* ssp. *kurstaki* SB4. These strains are used for control of lepidopteran larvae, but without noctuidae.

According to a further embodiment, the at least one pesticide II is selected from *Bacillus thuringiensis* subsp. *tenebrionis,* preferably the strains DSM 2803, NB-125 and NB-176, in particular NB-176, which all protect plants e.g. against leaf beetle larvae.

Preference is also given to mixtures comprising as pesticide II (component 2) a biopesticide from group L4), preferably selected from methyl jasmonate, *Acacia negra* extract, extract of grapefruit seeds and pulp, Catnip oil, Neem oil, Quillay extract and Tagetes oil, in particular methyl jasmonate or water-based Quillay extract.

Preference is also given to mixtures comprising as pesticide II (component 2) a biopesticide from group L5), preferably selected from *Azospirillum amazonense* BR 11140 (SpY2T), *A. brasilense* XOH, *A. brasilense* BR 11005 (Sp245), *A. brasilense* BR 11002, *A. lipoferum* BR 11646 (Sp31), *A. irakense, A. halopraeferens, Bacillus amyloliquefaciens* AP-136 (NRRL B-50614), *Bradyrhizobium* sp. (Vigna), *B. japonicum* USDA 3, *B. japonicum* USDA 31, *B. japonicum* USDA 76, *B. japonicum* USDA 110, *B. japonicum* USDA 121, *Glomus intraradices* RTI-801, *Paenibacillus alvei* NAS6G6, *Penicillium bilaiae, Rhizobium leguminosarum* bv. *phaseolii, R. l. trifolii, R. l.* bv. *viciae,* and *Sinorhizobium meliloti,* more preferably selected from *Azospirillum brasilense* BR 11005 (Sp245), *Bradyrhizobium* sp. (Vigna), *B. japonicum* USDA 3, *B. japonicum* USDA 31, *B. japonicum* USDA 76, *B. japonicum* USDA 110, *B. japonicum* USDA 121, *Rhizobium leguminosarum* bv. *phaseolii, R. l. trifolii* RP113-7, *R. l.* bv.*viciae* SU303, *R. l.* bv. *viciae* WSM1455, *R. tropici* SEMIA 4088 and *Sinorhizobium meliloti.*

According to another embodiment of the inventive mixtures, *Bradyrhizobium* sp. (meaning any *Bradyrhizobium* species and/or strain) as pesticide II is *Bradyrhizobium japonicum* (*B. japonicum*). These mixtures are particularly suitable in soybean. *B. japonicum* strains were cultivated using media and fermentation techniques known in the art, e.g. in yeast extract-mannitol broth (YEM) at 27° C. for about 5 days.

The present invention also relates to mixtures, wherein the at least one pesticide II is selected from *Bradyrhizobium japonicum* (*B. japonicum*) and further comprises a compound III, wherein compound III is selected from jasmonic acid or salts or derivatives thereof including cis-jasmone, preferably methyl-jasmonate or cis-jasmone.

References for various *B. japonicum* strains are given e.g. in U.S. Pat. No. 7,262,151 (*B. japonicum* strains USDA 110(=IITA 2121, SEMIA 5032, RCR 3427, ARS I-110, Nitragin 61A89; isolated from *Glycine max* in Florida in 1959, Serogroup 110; Appl Environ Microbiol 60, 940-94, 1994), USDA 31(=Nitragin 61A164; isolated from *Glycine max* in Wisoconsin in 1941, USA, Serogroup 31), USDA 76 (plant passage of strain USDA 74 which has been isolated from *Glycine max* in California, USA, in 1956, Serogroup 76), USDA 121 (isolated from *Glycine max* in Ohio, USA, in 1965), USDA 3 (isolated from *Glycine max* in Virginia, USA, in 1914, Serogroup 6), USDA 121 (Crop Science 26(5), 911-916, 1986) and USDA 136(=CB 1809, SEMIA 586, Nitragin 61A136, RCR 3407; isolated from *Glycine max* in Beltsville, Md. in 1961; Appl Environ Microbiol 60, 940-94, 1994). Further suitable *B. japonicum* strain G49 (INRA, Angers, France) is described in Fernandez-Flouret, D. & Cleyet-Marel, J. C. (1987) C R Acad Agric Fr 73, 163-171), especially for soybean grown in Europe, in particular in France. Further suitable *B. japonicum* strain TA-11 (TA11 NOD+) (NRRL B-18466) is i.a. described in U.S. Pat. No. 5,021,076; Appl Environ Microbiol (1990) 56, 2399-2403 and commercially available as liquid inoculant for soybean (VAULT® NP, Becker Underwood, USA). Further *B. japonicum* strains as example for pesticide 11 are described in US2012/0252672A. Further suitable and especially in Canada commercially available strain 532c (The Nitragin Company, Milwaukee, Wis., USA, field isolate from Wisconsin; Nitragin strain collection No. 61A152; Can J Plant Sci 70 (1990), 661-666) (e.g. in RHIZOFLO, HIS-TICK, HICOAT Super from Becker Underwood, Canada). Preferably, *B. japonicum* is selected from strains TA-11 and 532c, more preferably a mixture of *B. japonicum* strains TA-11 and 532c.

Other suitable and commercially available *B. japonicum* strains (see e.g. Appl Environ Microbiol 2007, 73(8), 2635) are SEMIA 566 (isolated from North American inoculant in 1966 and used in Brazilian commercial inoculants from 1966 to 1978), SEMIA 586(=CB 1809; originally isolated in Maryland, USA but received from Austrailia in 1966 and used in Brazilian inoculants in 1977), CPAC 15 (=SEMIA 5079; a natural varaiant of SEMIA 566 used in commercial inoculants since 1992) and CPAC 7(=SEMIA 5080; a natural variant of SEMIA 586 used in commercial inoculants since 1992). These strains are especially suitable for soybean grown in Australia or South America, in particular in Brazil. In particular, mixtures of *B. japonicum* SEMIA 5079 and SEMIA 5080 are suitable. Some of the abovementioned strains have been re-classified as a novel species *Bradyrhizobium elkanii,* e.g. strain USDA 76 (Can. J. Microbiol., 1992, 38, 501-505).

Another suitable and commercially available *B. japonicum* strain is E-109 (variant of strain USDA 138, see e.g. Eur. J. Soil Biol. 45 (2009) 28-35; Biol Fertil Soils (2011) 47:81-89, deposited at Agriculture Collection Laboratory of the Instituto de Microbiologia y Zoologia Agri cola (IMYZA), Instituto Nacional de Tecnologi'a Agropecuaria (INTA), Castelar, Argentina). This strain is especially suitable for soybean grown in South America, in particular in Argentina.

Another suitable and commercially available *B. japonicum* strain are WB74 or WB74-1 (e.g. from Stimuplant CC, South Africa or from SoyGro Bio-Fertilizer Ltd, South Africa). These strains are especially suitable for soybean grown in South America and Africa, in particular in South Africa.

The present invention also relates to mixtures, wherein the at least one pesticide II is selected from *Bradyrhizobium elkanii* and *Bradyrhizobium liaoningense* (*B. elkanii* and *B. liaoningense*), more preferably from *B. elkanii.* These mixtures are particularly suitable in soybean. *B. elkanii* and liaoningense were cultivated using media and fermentation techniques known in the art, e.g. in yeast extract-mannitol broth (YEM) at 27° C. for about 5 days.

The present invention also relates to mixtures wherein the at least one pesticide II is selected from selected from *B. elkanii* and *B. liaoningense* and further comprises a compound III, wherein compound III is selected from jasmonic acid or salts or derivatives thereof including cis-jasmone, preferably methyl-jasmonate or cis-jasmone.

Suitable and commercially available *B. elkanii* strains are SEMIA 587 and SEMIA 5019(=29W) (see e.g. Appl Environ Microbiol 2007, 73(8), 2635) and USDA 3254 and USDA 76 and USDA 94. Preferably, mixtures of *B. elkanii* strains SEMIA 587 and SEMIA 5019 are useful (e.g. in Gelfix 5 from Nitral Urbana Laboratories, Brazil, a BASF Company). Further commercially available *B. elkanii* strains are U-1301 and U-1302 (e.g. product Nitroagin® Optimize from Novozymes Bio As S.A., Brazil or NITRASEC for soybean from LACE y Cia, Brazil). These strains are especially suitable for soybean grown in Australia or South America, in particular in Brazil.

The present invention also relates to mixtures, wherein pesticide II is selected from *Bradyrhizobium* sp. (*Arachis*) (*B.* sp. *Arachis*) which shall describe the cowpea miscellany cross-inoculation group which includes inter alia indigenous cowpea bradyrhizobia on cowpea (*Vigna unguiculata*), siratro (*Macroptilium atropurpureum*), lima bean (*Phaseolus lunatus*), and peanut (*Arachis hypogaea*). This mixture comprising as pesticide II *B*. sp. *Arachis* is especially suitable for use in peanut, Cowpea, Mung bean, Moth bean, Dune bean, Rice bean, Snake bean and Creeping vigna, in particular peanut.

The present invention also relates to mixtures wherein the at least one pesticide II is selected from *B*. sp. (*Arachis*) and further comprises a compound III, wherein compound III is selected from jasmonic acid or salts or derivatives thereof including cis-jasmone, preferably methyl-jasmonate or cis-jasmone.

Suitable and commercially available *B*. sp. (*Arachis*) strain is CB1015 (=IITA 1006, USDA 3446 presumably originally collected in India; from Australian Inoculants Research Group. These strains are especially suitable for peanut grown in Australia, North America or South America, in particular in Brazil. Further suitable strain is *Bradyrhizobium* sp. PNL01 (Becker Underwood, Bisson and Mason, Apr. 29, 2010, Project report, Worcester Polytechnic Institute, Worcester, MA, USA).

Suitable and commercially available *Bradyrhizobium* sp. (*Arachis*) strains especially for cowpea and peanut but also for soybean are *Bradyrhizobium* SEMIA 6144, SEMIA 6462(=BR 3267) and SEMIA 6464(=BR 3262; see e.g. FEMS Microbiology Letters (2010) 303(2), 123-131; Revista Brasileira de Ciencia do Solo (2011) 35(3);739-742, ISSN 0100-0683).

The present invention also relates to mixtures, wherein the at least one pesticide II is selected from *Bradyrhizobium* sp. (Lupine) (also called *B. lupini, B. lupines* or *Rhizobium lupini*). This mixture is especially suitable for use in dry beans and lupins.

The present invention also relates to mixtures wherein the at least one pesticide II is selected from *Bradyrhizobium* sp. (*Lupine*) (*B. lupini*) and further comprises a compound III, wherein compound III is selected from jasmonic acid or salts or derivatives thereof including cis-jasmone, preferably methyl-jasmonate or cis-jasmone.

Suitable and commercially available *B. lupini* strain is LL13 (isolated from *Lupinus iuteus* nodules from French soils; deposited at INRA, Dijon and Angers, France. This strain is especially suitable for *lupins* grown in Australia, North America or Europe, in particular in Europe.

Further suitable and commercially available *B. lupini* strains WU425 (isolated in Esperance, Western Australia from a non-Australian legume *Ornthopus compressus*), WSM4024 (isolated from *lupins* in Australia by CRS during a 2005 survey) and WSM471 (isolated from *Ornithopus pinnatus* in Oyster Harbour, Western Australia) are described e.g. in Palta J.A. and Berger J.B. (eds), 2008, Proceedings 12th International Lupin Conference, 14-18 Sept. 2008, Fremantle, Western Australia. International Lupin Association, Canterbury, New Zealand, 47-50, ISBN 0-86476-153-8; Appl. Environ. Microbiol. 71, 7041-7052, 2005; Australian J. Exp. Agricult. 36(1), 63-70, 1996.

The present invention also relates to mixtures, wherein the at least one pesticide II is selected from *Mesorhizobium* sp. (meaning any *Mesorhizobium* species and/or strain), more preferably *Mesorhizobium ciceri*. These mixtures are particularly suitable in cowpea.

The present invention also relates to mixtures wherein the at least one pesticide II is selected from *Mesorhizobium* sp. and further comprises a compound III, wherein compound III is selected from jasmonic acid or salts or derivatives thereof including cis-jasmone, preferably methyl-jasmonate or cis-jasmone.

Suitable and commercially available *Mesorhizobium* sp. strains are e.g. *M. ciceri* CC1192(=UPM 848, CECT 5549; from Horticultural Research Station, Gosford, Australia; collected in Israel from *Cicer arietinum* nodules; Can J Microbial (2002) 48, 279-284) and *Mesorhizobium* sp. strains WSM1271 (collected in Sardinia, Italy, from plant host *Biserrula pelecinus*), WSM 1497 (collected in Mykonos, Greece, from plant host *Biserrula pelecinus*), *M. loti* strains CC829 (commerical inoculant for *Lotus peduncula- tus* and *L. ulginosus* in Australia, isolated from *L. ulginosus* nodules in USA; NZP 2012), *M. loti* SU343 (a commercial inoculant for *Lotus corniculatus* in Australia; isolated from host nodules in USA). For references see e.g. Soil Biol Biochem (2004) 36(8), 1309-1317; Plant and Soil (2011) 348(1-2), 231-243).

Suitable and commercially available *M. loti* strains are e.g. *M. loti* CC829 for *Lotus pedunculatus*.

The present invention also relates to mixtures wherein the at least one pesticide II is selected from *Mesorhizobium huakuii*, also referred to as *Rhizobium huakuii* (see e.g. Appl. Environ. Microbiol. 2011, 77(15), 5513-5516). These mixtures are particularly suitable in *Astralagus,* e.g. *Astalagus sinicus* (Chinese milkwetch), *Thermopsis,* e.g. *Thermopsis luinoides* (Goldenbanner) and alike.

The present invention also relates to mixtures wherein the at least one pesticide II is selected from *Mesorhizobium huakuii* and further comprises a compound III, wherein compound III is selected from jasmonic acid or salts or derivatives thereof including cis-jasmone, preferably methyl-jasmonate or cis-jasmone.

Suitable and commercially available *M. huakuii* strain is HN3015 which was isolated from *Astralagus sinicus* in a rice-growing field of Southern China (see e.g. World J. Microbiol. Biotechn. (2007) 23(6), 845-851, ISSN 0959-3993).

The present invention also relates to mixtures, wherein the at least one pesticide II is selected from *Azospirillum amazonense, A. brasilense, A. lipoferunn, A. irakense* and *A. halopraeferens,* more preferably from *A. brasilense,* in particular selected from *A. brasilense* strains BR 11005 (Sp245) and AZ39 which are both commercially used in Brazil and are obtainable from EMBRAPA-Agribiologia, Brazil. These mixtures are particularly suitable in soybean.

The present invention also relates to mixtures wherein the at least one pesticide II is selected from *A. amazonense, A. brasilense, A. lipoferunn, A. irakense* and *A. halopraeferens,* more preferably *A. brasilense,* and further comprises a compound III, wherein compound III is selected from jasmonic acid or salts or derivatives thereof including cis-jasmone, preferably methyl-jasmonate or cis-jasmone.

The present invention also relates to mixtures wherein the at least one pesticide II is selected from *Rhizobium leguminosarum* bv. *phaseolii; R. l. trifolii,* especially strain RP113-7 thereof, *R. l.* bv. *viciae,* in particular strains SU303, WSM1455 and P1NP3Cst thereof; *R. tropici,* especially strain SEMIA 4088 thereof; and *Sinorhizobium meliloti,* especially strain MSDJ0848 thereof. *Sinorhizobium meliloti* is commercially available from Becker Underwood as product Dormal® Alfalfa & Luzerne. *Rhizobium leguminosarum* bv. *phaseoli* is commercially available from Becker Underwood as product Rhizo Stick. These strains are particularly suitable as inoculants for various legumes such as alfalfa, clover, peas, beans, lentils, soybeans, peanuts and others.

The present invention also relates to mixtures wherein the at least one pesticide II is selected from *R. leguminosarum* bv. *phaseolii, R. l. trifolii, R. l.* bv. *viciae, R. tropici* and *Sinorhizobium meliloti,* and further comprises a compound III, wherein compound III is selected from jasmonic acid or salts or derivatives thereof including cis-jasmone, preferably methyl-jasmonate or cis-jasmone.

According to a further embodiment, the at least one pesticide II is selected from *Delftia acidovorans,* in particular strain RAY209, especially in soybean and canola.

According to a further embodiment, the at least one pesticide II is selected from *Lysobacter* spp., preferably selected from *L. antibioticus,* in particular strains 13-1 and HS124, preferably in rice or pepper for control of *Phytophthora* or bacterial leaf blight. According to a further embodiment, the at least one pesticide II is selected from *L. enzymogenes,* in particular strain 3.1T8.

According to a further embodiment, the at least one pesticide II is selected from *Lysobacter* spp., preferably selected from *Pseudomonas* spp., in particular strain MA 342 and *Pseudomonas* sp. DSM 13134.

According to a further embodiment, the at least one pesticide II is selected from *Penicillium bilaiae.*

Preference is also given to mixtures comprising as pesticide II (component 2) a biopesticide from group L6), preferably selected from abscisic acid, aluminium silicate (kaolin), humates, *Ascophyllum nodosum* (Norwegian kelp, Brown kelp) extract and *Ecklonia maxima* (kelp) extract.

Preference is also given to mixtures comprising as pesticide II a biopesticide selected from the isoflavones formonennitin, hesperetin and naringenin.

Accordingly, the present invention furthermore relates to compositions comprising a strain, cell-free extract, culture medium or extrolite of the invention (component 1) and one pesticide II (component 2), which pesticide II is selected from the column "Co. 2" of the lines B-1 to B-810 of Table B.

A further embodiment relates to the compositions B-1 to B-810 listed in Table B, where a row of Table B corresponds in each case to a fungicidal composition comprising as active components one of the in the present specification individualized compounds of formula I (component 1) and the respective pesticide II from groups A) to O) (component 2) stated in the row in question. Preferably, the compositions described comprise the active components in synergistically effective amounts.

TABLE B

Compositions comprising as active components one indivivalized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-1 | (I) | (A.1.1) |
| B-2 | (I) | (A.1.2) |
| B-3 | (I) | (A.1.3) |
| B-4 | (I) | (A.1.4) |
| B-5 | (I) | (A.1.5) |
| B-6 | (I) | (A.1.6) |
| B-7 | (I) | (A.1.7) |
| B-8 | (I) | (A.1.8) |
| B-9 | (I) | (A.1.9) |
| B-10 | (I) | (A.1.10) |
| B-11 | (I) | (A.1.11) |
| B-12 | (I) | (A.1.12) |
| B-13 | (I) | (A.1.13) |
| B-14 | (I) | (A.1.14) |
| B-15 | (I) | (A.1.15) |
| B-16 | (I) | (A.1.16) |
| B-17 | (I) | (A.1.17) |
| B-18 | (I) | (A.1.18) |
| B-19 | (I) | (A.1.19) |
| B-20 | (I) | (A.1.20) |
| B-21 | (I) | (A.1.21) |
| B-22 | (I) | (A.2.1) |
| B-23 | (I) | (A.2.2) |
| B-24 | (I) | (A.2.3) |
| B-25 | (I) | (A.2.4) |
| B-26 | (I) | (A.2.5) |
| B-27 | (I) | (A.2.6) |
| B-28 | (I) | (A.2.7) |
| B-29 | (I) | (A.3.1) |
| B-30 | (I) | (A.3.2) |
| B-31 | (I) | (A.3.3) |
| B-32 | (I) | (A.3.4) |
| B-33 | (I) | (A.3.5) |
| B-34 | (I) | (A.3.6) |
| B-35 | (I) | (A.3.7) |
| B-36 | (I) | (A.3.8) |
| B-37 | (I) | (A.3.9) |
| B-38 | (I) | (A.3.10) |
| B-39 | (I) | (A.3.11) |
| B-40 | (I) | (A.3.12) |
| B-41 | (I) | (A.3.13) |
| B-42 | (I) | (A.3.14) |
| B-43 | (I) | (A.3.15) |
| B-44 | (I) | (A.3.16) |
| B-45 | (I) | (A.3.17) |
| B-46 | (I) | (A.3.18) |

TABLE B-continued

Compositions comprising as active components one indivizalized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-47 | (I) | (A.3.19) |
| B-48 | (I) | (A.3.20) |
| B-49 | (I) | (A.3.21) |
| B-50 | (I) | (A.3.22) |
| B-51 | (I) | (A.3.23) |
| B-52 | (I) | (A.3.24) |
| B-53 | (I) | (A.3.25) |
| B-54 | (I) | (A.3.26) |
| B-55 | (I) | (A.3.27) |
| B-56 | (I) | (A.4.1) |
| B-57 | (I) | (A.4.2) |
| B-58 | (I) | (A.4.3) |
| B-59 | (I) | (A.4.4) |
| B-60 | (I) | (A.4.5) |
| B-61 | (I) | (A.4.6) |
| B-62 | (I) | (A.4.7) |
| B-63 | (I) | (A.4.8) |
| B-64 | (I) | (A.4.9) |
| B-65 | (I) | (A.4.10) |
| B-66 | (I) | (A.4.11) |
| B-67 | (I) | (A.4.12) |
| B-68 | (I) | (B.1.1) |
| B-69 | (I) | (B.1.2) |
| B-70 | (I) | (B.1.3) |
| B-71 | (I) | (B.1.4) |
| B-72 | (I) | (B.1.5) |
| B-73 | (I) | (B.1.6) |
| B-74 | (I) | (B.1.7) |
| B-75 | (I) | (B.1.8) |
| B-76 | (I) | (B.1.9) |
| B-77 | (I) | (B.1.10) |
| B-78 | (I) | (B.1.11) |
| B-79 | (I) | (B.1.12) |
| B-80 | (I) | (B.1.13) |
| B-81 | (I) | (B.1.14) |
| B-82 | (I) | (B.1.15) |
| B-83 | (I) | (B.1.16) |
| B-84 | (I) | (B.1.17) |
| B-85 | (I) | (B.1.18) |
| B-86 | (I) | (B.1.19) |
| B-87 | (I) | (B.1.20) |
| B-88 | (I) | (B.1.21) |
| B-89 | (I) | (B.1.22) |
| B-90 | (I) | (B.1.23) |
| B-91 | (I) | (B.1.24) |
| B-92 | (I) | (B.1.25) |
| B-93 | (I) | (B.1.26) |
| B-94 | (I) | (B.1.27) |
| B-95 | (I) | (B.1.28) |
| B-96 | (I) | (B.1.29) |
| B-97 | (I) | (B.1.30) |
| B-98 | (I) | (B.1.31) |
| B-99 | (I) | (B.1.32) |
| B-100 | (I) | (B.1.33) |
| B-101 | (I) | (B.1.34) |
| B-102 | (I) | (B.1.35) |
| B-103 | (I) | (B.1.36) |
| B-104 | (I) | (B.1.37) |
| B-105 | (I) | (B.1.38) |
| B-106 | (I) | (B.1.39) |
| B-107 | (I) | (B.1.40) |
| B-108 | (I) | (B.1.41) |
| B-109 | (I) | (B.1.42) |
| B-110 | (I) | (B.1.43) |
| B-111 | (I) | (B.1.44) |
| B-112 | (I) | (B.1.45) |
| B-113 | (I) | (B.1.46) |
| B-114 | (I) | (B.1.47) |
| B-115 | (I) | (B.1.48) |
| B-116 | (I) | (B.1.49) |
| B-117 | (I) | (B.1.50) |
| B-118 | (I) | (B.2.1) |
| B-119 | (I) | (B.2.2) |

TABLE B-continued

Compositions comprising as active components one indivialized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-120 | (I) | (B.2.3) |
| B-121 | (I) | (B.2.4) |
| B-122 | (I) | (B.2.5) |
| B-123 | (I) | (B.2.6) |
| B-124 | (I) | (B.2.7) |
| B-125 | (I) | (B.2.8) |
| B-126 | (I) | (B.3.1) |
| B-127 | (I) | (C.1.1) |
| B-128 | (I) | (C.1.2) |
| B-129 | (I) | (C.1.3) |
| B-130 | (I) | (C.1.4) |
| B-131 | (I) | (C.1.5) |
| B-132 | (I) | (C.1.6) |
| B-133 | (I) | (C.1.7) |
| B-134 | (I) | (C.2.1) |
| B-135 | (I) | (C.2.2) |
| B-136 | (I) | (C.2.3) |
| B-137 | (I) | (C.2.4) |
| B-138 | (I) | (C.2.5) |
| B-139 | (I) | (C.2.6) |
| B-140 | (I) | (C.2.7) |
| B-141 | (I) | (D.1.1) |
| B-142 | (I) | (D.1.2) |
| B-143 | (I) | (D.1.3) |
| B-144 | (I) | (D.1.4) |
| B-145 | (I) | (D.1.5) |
| B-146 | (I) | (D.1.6) |
| B-147 | (I) | (D.2.1) |
| B-148 | (I) | (D.2.2) |
| B-149 | (I) | (D.2.3) |
| B-150 | (I) | (D.2.4) |
| B-151 | (I) | (D.2.5) |
| B-152 | (I) | (D.2.6) |
| B-153 | (I) | (D.2.7) |
| B-154 | (I) | (E.1.1) |
| B-155 | (I) | (E.1.2) |
| B-156 | (I) | (E.1.3) |
| B-157 | (I) | (E.2.1) |
| B-158 | (I) | (E.2.2) |
| B-159 | (I) | (E.2.3) |
| B-160 | (I) | (E.2.4) |
| B-161 | (I) | (E.2.5) |
| B-162 | (I) | (E.2.6) |
| B-163 | (I) | (E.2.7) |
| B-164 | (I) | (E.2.8) |
| B-165 | (I) | (F.1.1) |
| B-166 | (I) | (F.1.2) |
| B-167 | (I) | (F.1.3) |
| B-168 | (I) | (F.1.4) |
| B-169 | (I) | (F.1.5) |
| B-170 | (I) | (F.1.6) |
| B-171 | (I) | (F.2.1) |
| B-172 | (I) | (G.1.1) |
| B-173 | (I) | (G.1.2) |
| B-174 | (I) | (G.1.3) |
| B-175 | (I) | (G.1.4) |
| B-176 | (I) | (G.2.1) |
| B-177 | (I) | (G.2.2) |
| B-178 | (I) | (G.2.3) |
| B-179 | (I) | (G.2.4) |
| B-180 | (I) | (G.2.5) |
| B-181 | (I) | (G.2.6) |
| B-182 | (I) | (G.2.7) |
| B-183 | (I) | (G.3.1) |
| B-184 | (I) | (G.3.2) |
| B-185 | (I) | (G.3.3) |
| B-186 | (I) | (G.3.4) |
| B-187 | (I) | (G.3.5) |
| B-188 | (I) | (G.3.6) |
| B-189 | (I) | (G.3.7) |
| B-190 | (I) | (G.3.8) |
| B-191 | (I) | (G.4.1) |
| B-192 | (I) | (G.5.1) |

TABLE B-continued

Compositions comprising as active components one indivualized strain, cell-free extract, culture medium or extrolite of the TABLE B-continued Compositions comprising as active components one indivualized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
| --- | --- | --- |
| B-266 | (I) | (K.1.22) |
| B-267 | (I) | (K.1.23) |
| B-268 | (I) | (K.1.24) |
| B-269 | (I) | (K.1.25) |
| B-270 | (I) | (K.1.26) |
| B-271 | (I) | (K.1.27) |
| B-272 | (I) | (K.1.28) |
| B-273 | (I) | (K.1.29) |
| B-274 | (I) | (K.1.30) |
| B-275 | (I) | (K.1.31) |
| B-276 | (I) | (K.1.32) |
| B-277 | (I) | (K.1.33) |
| B-278 | (I) | (K.1.34) |
| B-279 | (I) | (K.1.35) |
| B-280 | (I) | (K.1.36) |
| B-281 | (I) | (K.1.37) |
| B-282 | (I) | (K.1.38) |
| B-283 | (I) | (K.1.39) |
| B-284 | (I) | (K.1.40) |
| B-285 | (I) | (K.1.41) |
| B-286 | (I) | (K.1.42) |
| B-287 | (I) | (K.1.43) |
| B-288 | (I) | (K.1.44) |
| B-289 | (I) | (K.1.45) |
| B-290 | (I) | (K.1.46) |
| B-291 | (I) | (K.1.47) |
| B-292 | (I) | (M.1.1) |
| B-293 | (I) | (M.1.2) |
| B-294 | (I) | (M.1.3) |
| B-295 | (I) | (M.1.4) |
| B-296 | (I) | (M.1.5) |
| B-297 | (I) | (M.1.6) |
| B-298 | (I) | (M.1.7) |
| B-299 | (I) | (M.1.8) |
| B-300 | (I) | (M.1.9) |
| B-301 | (I) | (M.1.10) |
| B-302 | (I) | (M.1.11) |
| B-303 | (I) | (M.1.12) |
| B-304 | (I) | (M.1.13) |
| B-305 | (I) | (M.1.14) |
| B-306 | (I) | (M.1.15) |
| B-307 | (I) | (M.1.16) |
| B-308 | (I) | (M.1.17) |
| B-309 | (I) | (M.1.18) |
| B-310 | (I) | (M.1.19) |
| B-311 | (I) | (M.1.20) |
| B-312 | (I) | (M.1.21) |
| B-313 | (I) | (M.1.22) |
| B-314 | (I) | (M.1.23) |
| B-315 | (I) | (M.1.24) |
| B-316 | (I) | (M.1.25) |
| B-317 | (I) | (M.1.26) |
| B-318 | (I) | (M.1.27) |
| B-319 | (I) | (M.1.28) |
| B-320 | (I) | (M.1.29) |
| B-321 | (I) | (M.1.30) |
| B-322 | (I) | (M.1.31) |
| B-323 | (I) | (M.1.32) |
| B-324 | (I) | (M.1.33) |
| B-325 | (I) | (M.1.34) |
| B-326 | (I) | (M.1.35) |
| B-327 | (I) | (M.1.36) |
| B-328 | (I) | (M.1.37) |
| B-329 | (I) | (M.1.38) |
| B-330 | (I) | (M.1.39) |
| B-331 | (I) | (M.1.40) |
| B-332 | (I) | (M.1.41) |
| B-333 | (I) | (M.1.42) |
| B-334 | (I) | (M.1.43) |
| B-335 | (I) | (M.1.44) |
| B-336 | (I) | (M.1.45) |
| B-337 | (I) | (M.1.46) |
| B-338 | (I) | (M.1.47) |

TABLE B-continued

Compositions comprising as active components one indivialized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-339 | (I) | (M.1.48) |
| B-340 | (I) | (M.1.49) |
| B-341 | (I) | (M.1.50) |
| B-342 | (I) | (N.1.1) |
| B-343 | (I) | (N.1.2) |
| B-344 | (I) | (N.1.3) |
| B-345 | (I) | (N.1.4) |
| B-346 | (I) | (N.1.5) |
| B-347 | (I) | (N.2.1) |
| B-348 | (I) | (N.2.2) |
| B-349 | (I) | (N.2.3) |
| B-350 | (I) | (N.3.1) |
| B-351 | (I) | (N.3.2) |
| B-352 | (I) | (N.3.3) |
| B-353 | (I) | (N.3.4) |
| B-354 | (I) | (N.4.1) |
| B-355 | (I) | (N.5.1) |
| B-356 | (I) | (N.6.1) |
| B-357 | (I) | (N.6.2) |
| B-358 | (I) | (N.6.3) |
| B-359 | (I) | (N.6.4) |
| B-360 | (I) | (N.6.5) |
| B-361 | (I) | (N.7.1) |
| B-362 | (I) | (N.7.2) |
| B-363 | (I) | (N.7.3) |
| B-364 | (I) | (N.8.1) |
| B-365 | (I) | (N.9.1) |
| B-366 | (I) | (N.10.1) |
| B-367 | (I) | (N.10.2) |
| B-368 | (I) | (N.10.3) |
| B-369 | (I) | (N.10.4) |
| B-370 | (I) | (N.10.5) |
| B-371 | (I) | (N.11.1) |
| B-372 | (I) | (N.12.1) |
| B-373 | (I) | (N.12.2) |
| B-374 | (I) | (N.12.3) |
| B-375 | (I) | (N.12.4) |
| B-376 | (I) | (N.13.1) |
| B-377 | (I) | (N.13.2) |
| B-378 | (I) | (N.13.3) |
| B-379 | (I) | (N.13.4) |
| B-380 | (I) | (N.13.5) |
| B-381 | (I) | (N.13.6) |
| B-382 | (I) | (N.13.7) |
| B-383 | (I) | (N.13.8) |
| B-384 | (I) | (N.13.9) |
| B-385 | (I) | (N.14.1) |
| B-386 | (I) | (N.14.2) |
| B-387 | (I) | (N.15.1) |
| B-388 | (I) | (N.16.1) |
| B-389 | (I) | (N.16.2) |
| B-390 | (I) | (N.17.1) |
| B-391 | (I) | (N.17.2) |
| B-392 | (I) | (N.17.3) |
| B-393 | (I) | (N.17.4) |
| B-394 | (I) | (N.17.5) |
| B-395 | (I) | (N.17.6) |
| B-396 | (I) | (N.17.7) |
| B-397 | (I) | (N.17.8) |
| B-398 | (I) | (N.17.9) |
| B-399 | (I) | (N.17.10) |
| B-400 | (I) | (N.17.11) |
| B-401 | (I) | (N.17.12) |
| B-402 | (I) | (O.1.1) |
| B-403 | (I) | (O.1.2) |
| B-404 | (I) | (O.1.3) |
| B-405 | (I) | (O.1.4) |
| B-406 | (I) | (O.1.5) |
| B-407 | (I) | (O.1.6) |
| B-408 | (I) | (O.1.7) |
| B-409 | (I) | (O.1.8) |
| B-410 | (I) | (O.1.9) |
| B-411 | (I) | (O.1.10) |

TABLE B-continued

Compositions comprising as active components one indivialized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-412 | (I) | (O.1.11) |
| B-413 | (I) | (O.1.12) |
| B-414 | (I) | (O.1.13) |
| B-415 | (I) | (O.1.14) |
| B-416 | (I) | (O.1.15) |
| B-417 | (I) | (O.1.16) |
| B-418 | (I) | (O.1.17) |
| B-419 | (I) | (O.1.18) |
| B-420 | (I) | (O.1.19) |
| B-421 | (I) | (O.1.20) |
| B-422 | (I) | (O.1.21) |
| B-423 | (I) | (O.1.22) |
| B-424 | (I) | (O.1.23) |
| B-425 | (I) | (O.1.24) |
| B-426 | (I) | (O.1.25) |
| B-427 | (I) | (O.1.26) |
| B-428 | (I) | (O.1.27) |
| B-429 | (I) | (O.1.28) |
| B-430 | (I) | (O.1.29) |
| B-431 | (I) | (O.1.30) |
| B-432 | (I) | (O.1.31) |
| B-433 | (I) | (O.1.32) |
| B-434 | (I) | (O.1.33) |
| B-435 | (I) | (O.1.34) |
| B-436 | (I) | (O.1.35) |
| B-437 | (I) | (O.1.36) |
| B-438 | (I) | (O.1.37) |
| B-439 | (I) | (O.1.38) |
| B-440 | (I) | (O.2.1) |
| B-441 | (I) | (O.2.2) |
| B-442 | (I) | (O.2.3) |
| B-443 | (I) | (O.2.4) |
| B-444 | (I) | (O.2.5) |
| B-445 | (I) | (O.2.6) |
| B-446 | (I) | (O.2.7) |
| B-447 | (I) | (O.2.8) |
| B-448 | (I) | (O.2.9) |
| B-449 | (I) | (O.2.10) |
| B-450 | (I) | (O.2.11) |
| B-451 | (I) | (O.2.12) |
| B-452 | (I) | (O.2.13) |
| B-453 | (I) | (O.2.14) |
| B-454 | (I) | (O.2.15) |
| B-455 | (I) | (O.2.16) |
| B-456 | (I) | (O.3.1) |
| B-457 | (I) | (O.3.2) |
| B-458 | (I) | (O.3.3) |
| B-459 | (I) | (O.3.4) |
| B-460 | (I) | (O.3.5) |
| B-461 | (I) | (O.3.6) |
| B-462 | (I) | (O.3.7) |
| B-463 | (I) | (O.3.8) |
| B-464 | (I) | (O.3.9) |
| B-465 | (I) | (O.3.10) |
| B-466 | (I) | (O.3.11) |
| B-467 | (I) | (O.3.12) |
| B-468 | (I) | (O.3.13) |
| B-469 | (I) | (O.3.14) |
| B-470 | (I) | (O.3.15) |
| B-471 | (I) | (O.3.16) |
| B-472 | (I) | (O.3.17) |
| B-473 | (I) | (O.3.18) |
| B-474 | (I) | (O.3.19) |
| B-475 | (I) | (O.3.20) |
| B-476 | (I) | (O.3.21) |
| B-477 | (I) | (O.3.22) |
| B-478 | (I) | (O.3.23) |
| B-479 | (I) | (O.3.24) |
| B-480 | (I) | (O.3.25) |
| B-481 | (I) | (O.3.26) |
| B-482 | (I) | (O.3.27) |
| B-483 | (I) | (O.4.1) |
| B-484 | (I) | (O.4.2) |

TABLE B-continued

Compositions comprising as active components one indivualized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-485 | (I) | (O.4.3) |
| B-486 | (I) | (O.4.4) |
| B-487 | (I) | (O.4.5) |
| B-488 | (I) | (O.4.6) |
| B-489 | (I) | (O.4.7) |
| B-490 | (I) | (O.4.8) |
| B-491 | (I) | (O.4.9) |
| B-492 | (I) | (O.4.10) |
| B-493 | (I) | (O.4.11) |
| B-494 | (I) | (O.4.12) |
| B-495 | (I) | (O.4.13) |
| B-496 | (I) | (O.4.14) |
| B-497 | (I) | (O.4.15) |
| B-498 | (I) | (O.4.16) |
| B-499 | (I) | (O.4.17) |
| B-500 | (I) | (O.4.18) |
| B-501 | (I) | (O.4.19) |
| B-502 | (I) | (O.4.20) |
| B-503 | (I) | (O.4.21) |
| B-504 | (I) | (O.4.22) |
| B-505 | (I) | (O.4.23) |
| B-506 | (I) | (O.4.24) |
| B-507 | (I) | (O.5.1) |
| B-508 | (I) | (O.5.2) |
| B-509 | (I) | (O.5.3) |
| B-510 | (I) | (O.5.4) |
| B-511 | (I) | (O.5.5) |
| B-512 | (I) | (O.5.6) |
| B-513 | (I) | (O.5.7) |
| B-514 | (I) | (O.5.8) |
| B-515 | (I) | (O.5.9) |
| B-516 | (I) | (O.6.1) |
| B-517 | (I) | (O.6.2) |
| B-518 | (I) | (O.6.3) |
| B-519 | (I) | (O.6.4) |
| B-520 | (I) | (O.6.5) |
| B-521 | (I) | (O.6.6) |
| B-522 | (I) | (O.6.7) |
| B-523 | (I) | (O.7.1) |
| B-524 | (I) | (O.7.2) |
| B-525 | (I) | (O.7.3) |
| B-526 | (I) | (O.7.4) |
| B-527 | (I) | (O.7.5) |
| B-528 | (I) | (O.7.6) |
| B-529 | (I) | (O.8.1) |
| B-530 | (I) | (O.8.2) |
| B-531 | (I) | (O.8.3) |
| B-532 | (I) | (O.8.4) |
| B-533 | (I) | (O.8.5) |
| B-534 | (I) | (O.9.1) |
| B-535 | (I) | (O.9.2) |
| B-536 | (I) | (O.9.3) |
| B-537 | (I) | (O.10.1) |
| B-538 | (I) | (O.11.1) |
| B-539 | (I) | (O.11.2) |
| B-540 | (I) | (O.11.3) |
| B-541 | (I) | (O.11.4) |
| B-542 | (I) | (O.12.1) |
| B-543 | (I) | (O.13.1) |
| B-544 | (I) | (O.14.1) |
| B-545 | (I) | (O.14.2) |
| B-546 | (I) | (O.15.1) |
| B-547 | (I) | (O.15.2) |
| B-548 | (I) | (O.15.3) |
| B-549 | (I) | (O.15.4) |
| B-550 | (I) | (O.15.5) |
| B-551 | (I) | (O.15.6) |
| B-552 | (I) | (O.15.7) |
| B-553 | (I) | (O.15.8) |
| B-554 | (I) | (O.15.9) |
| B-555 | (I) | (O.15.10) |
| B-556 | (I) | (O.15.11) |
| B-557 | (I) | (O.16.1) |

TABLE B-continued

Compositions comprising as active components one indivivalized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-558 | (I) | (O.16.2) |
| B-559 | (I) | (O.16.3) |
| B-560 | (I) | (O.16.4) |
| B-561 | (I) | (O.16.5) |
| B-562 | (I) | (O.16.6) |
| B-563 | (I) | (L.1.1) |
| B-564 | (I) | (L.1.2) |
| B-565 | (I) | (L.1.3) |
| B-566 | (I) | (L.1.4) |
| B-567 | (I) | (L.1.5) |
| B-568 | (I) | (L.1.6) |
| B-569 | (I) | (L.1.7) |
| B-570 | (I) | (L.1.8) |
| B-5/1 | (I) | (L.1.8) |
| B-572 | (I) | (L.1.10) |
| B-573 | (I) | (L.1.11) |
| B-574 | (I) | (L.1.12) |
| B-575 | (I) | (L.1.13) |
| B-576 | (I) | (L.1.14) |
| B-577 | (I) | (L.1.15) |
| B-578 | (I) | (L.1.16) |
| B-579 | (I) | (L.1.17) |
| B-580 | (I) | (L.1.18) |
| B-581 | (I) | (L.1.19) |
| B-582 | (I) | (L.1.20) |
| B-583 | (I) | (L.1.21) |
| B-584 | (I) | (L.1.22) |
| B-585 | (I) | (L.1.23) |
| B-586 | (I) | (L.1.24) |
| B-587 | (I) | (L.1.25) |
| B-588 | (I) | (L.1.26) |
| B-589 | (I) | (L.1.27) |
| B-590 | (I) | (L.1.28) |
| B-591 | (I) | (L.1.29) |
| B-592 | (I) | (L.1.30) |
| B-593 | (I) | (L.1.31) |
| B-594 | (I) | (L.1.32) |
| B-595 | (I) | (L.1.33) |
| B-596 | (I) | (L.1.34) |
| B-597 | (I) | (L.1.35) |
| B-598 | (I) | (L.1.36) |
| B-599 | (I) | (L.1.37) |
| B-600 | (I) | (L.1.38) |
| B-601 | (I) | (L.1.39) |
| B-602 | (I) | (L.1.40) |
| B-603 | (I) | (L.1.41) |
| B-604 | (I) | (L.1.42) |
| B-605 | (I) | (L.1.43) |
| B-606 | (I) | (L.1.44) |
| B-607 | (I) | (L.1.45) |
| B-608 | (I) | (L.1.46) |
| B-609 | (I) | (L.1.47) |
| B-610 | (I) | (L.1.48) |
| B-611 | (I) | (L.1.49) |
| B-612 | (I) | (L.1.50) |
| B-613 | (I) | (L.1.51) |
| B-614 | (I) | (L.1.52) |
| B-615 | (I) | (L.1.53) |
| B-616 | (I) | (L.1.54) |
| B-617 | (I) | (L.1.55) |
| B-618 | (I) | (L.1.56) |
| B-619 | (I) | (L.1.57) |
| B-620 | (I) | (L.1.58) |
| B-621 | (I) | (L.1.59) |
| B-622 | (I) | (L.1.60) |
| B-623 | (I) | (L.1.61) |
| B-624 | (I) | (L.1.62) |
| B-625 | (I) | (L.1.63) |
| B-626 | (I) | (L.1.64) |
| B-627 | (I) | (L.1.65) |
| B-628 | (I) | (L.1.66) |
| B-629 | (I) | (L.1.67) |
| B-630 | (I) | (L.1.68) |

TABLE B-continued

Compositions comprising as active components one indivialized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-631 | (I) | (L.1.69) |
| B-632 | (I) | (L.1.70) |
| B-633 | (I) | (L.1.71) |
| B-634 | (I) | (L.1.72) |
| B-635 | (I) | (L.1.73) |
| B-636 | (I) | (L.2.1) |
| B-637 | (I) | (L.2.2) |
| B-638 | (I) | (L.2.3) |
| B-639 | (I) | (L.2.4) |
| B-640 | (I) | (L.2.5) |
| B-641 | (I) | (L.2.6) |
| B-642 | (I) | (L.2.7) |
| B-643 | (I) | (L.2.8) |
| B-644 | (I) | (L.2.9) |
| B-645 | (I) | (L.2.10) |
| B-646 | (I) | (L.2.11) |
| B-647 | (I) | (L.3.1) |
| B-648 | (I) | (L.3.2) |
| B-649 | (I) | (L.3.3) |
| B-650 | (I) | (L.3.4) |
| B-651 | (I) | (L.3.5) |
| B-652 | (I) | (L.3.6) |
| B-653 | (I) | (L.3.7) |
| B-654 | (I) | (L.3.8) |
| B-655 | (I) | (L.3.9) |
| B-656 | (I) | (L.3.10) |
| B-657 | (I) | (L.3.11) |
| B-658 | (I) | (L.3.12) |
| B-659 | (I) | (L.3.13) |
| B-660 | (I) | (L.3.14) |
| B-661 | (I) | (L.3.15) |
| B-662 | (I) | (L.3.16) |
| B-663 | (I) | (L.3.17) |
| B-664 | (I) | (L.3.18) |
| B-665 | (I) | (L.3.19) |
| B-666 | (I) | (L.3.20) |
| B-667 | (I) | (L.3.21) |
| B-668 | (I) | (L.3.22) |
| B-669 | (I) | (L.3.23) |
| B-670 | (I) | (L.3.24) |
| B-671 | (I) | (L.3.25) |
| B-672 | (I) | (L.3.26) |
| B-673 | (I) | (L.3.27) |
| B-674 | (I) | (L.3.28) |
| B-675 | (I) | (L.3.29) |
| B-676 | (I) | (L.3.30) |
| B-677 | (I) | (L.3.31) |
| B-678 | (I) | (L.3.32) |
| B-679 | (I) | (L.3.33) |
| B-680 | (I) | (L.3.34) |
| B-681 | (I) | (L.3.35) |
| B-682 | (I) | (L.3.36) |
| B-683 | (I) | (L.3.37) |
| B-684 | (I) | (L.3.38) |
| B-685 | (I) | (L.3.39) |
| B-686 | (I) | (L.3.40) |
| B-687 | (I) | (L.3.41) |
| B-688 | (I) | (L.3.42) |
| B-689 | (I) | (L.3.43) |
| B-690 | (I) | (L.3.44) |
| B-691 | (I) | (L.3.45) |
| B-692 | (I) | (L.3.46) |
| B-693 | (I) | (L.3.47) |
| B-694 | (I) | (L.3.48) |
| B-695 | (I) | (L.3.49) |
| B-696 | (I) | (L.3.50) |
| B-697 | (I) | (L.3.51) |
| B-698 | (I) | (L.3.52) |
| B-699 | (I) | (L.3.53) |
| B-700 | (I) | (L.3.54) |
| B-701 | (I) | (L.3.55) |
| B-702 | (I) | (L.4.1) |
| B-703 | (I) | (L.4.2) |

TABLE B-continued

Compositions comprising as active components one indivualized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-704 | (I) | (L.4.3) |
| B-705 | (I) | (L.4.4) |
| B-706 | (I) | (L.4.5) |
| B-707 | (I) | (L.4.6) |
| B-708 | (I) | (L.4.7) |
| B-709 | (I) | (L.4.8) |
| B-710 | (I) | (L.4.9) |
| B-711 | (I) | (L.4.10) |
| B-712 | (I) | (L.4.11) |
| B-713 | (I) | (L.4.12) |
| B-714 | (I) | (L.4.13) |
| B-715 | (I) | (L.4.14) |
| B-716 | (I) | (L.4.15) |
| B-717 | (I) | (L.4.16) |
| B-718 | (I) | (L.4.17) |
| B-719 | (I) | (L.4.18) |
| B-720 | (I) | (L.4.19) |
| B-721 | (I) | (L.4.20) |
| B-722 | (I) | (L.4.21) |
| B-723 | (I) | (L.4.22) |
| B-724 | (I) | (L.4.23) |
| B-725 | (I) | (L.4.24) |
| B-726 | (I) | (L.4.25) |
| B-727 | (I) | (L.4.26) |
| B-728 | (I) | (L.4.27) |
| B-729 | (I) | (L.4.28) |
| B-730 | (I) | (L.4.29) |
| B-731 | (I) | (L.4.30) |
| B-732 | (I) | (L.4.31) |
| B-733 | (I) | (L.4.32) |
| B-734 | (I) | (L.4.33) |
| B-735 | (I) | (L.5.1) |
| B-736 | (I) | (L.5.2) |
| B-737 | (I) | (L.5.3) |
| B-738 | (I) | (L.5.4) |
| B-739 | (I) | (L.5.5) |
| B-740 | (I) | (L.5.6) |
| B-741 | (I) | (L.5.7) |
| B-742 | (I) | (L.5.8) |
| B-743 | (I) | (L.5.9) |
| B-744 | (I) | (L.5.10) |
| B-745 | (I) | (L.5.11) |
| B-746 | (I) | (L.5.12) |
| B-747 | (I) | (L.5.13) |
| B-748 | (I) | (L.5.14) |
| B-749 | (I) | (L.5.15) |
| B-750 | (I) | (L.5.16) |
| B-751 | (I) | (L.5.17) |
| B-752 | (I) | (L.5.18) |
| B-753 | (I) | (L.5.19) |
| B-754 | (I) | (L.5.20) |
| B-755 | (I) | (L.5.21) |
| B-756 | (I) | (L.5.22) |
| B-757 | (I) | (L.5.23) |
| B-758 | (I) | (L.5.24) |
| B-759 | (I) | (L.5.25) |
| B-760 | (I) | (L.5.26) |
| B-761 | (I) | (L.5.27) |
| B-762 | (I) | (L.5.28) |
| B-763 | (I) | (L.5.29) |
| B-764 | (I) | (L.5.30) |
| B-765 | (I) | (L.5.31) |
| B-766 | (I) | (L.5.32) |
| B-767 | (I) | (L.5.33) |
| B-768 | (I) | (L.5.34) |
| B-769 | (I) | (L.5.35) |
| B-770 | (I) | (L.5.36) |
| B-771 | (I) | (L.5.37) |
| B-772 | (I) | (L.5.38) |
| B-773 | (I) | (L.5.39) |
| B-774 | (I) | (L.5.40) |
| B-775 | (I) | (L.5.41) |
| B-776 | (I) | (L.5.42) |

TABLE B-continued

Compositions comprising as active components one indivivalized strain, cell-free extract, culture medium or extrolite of the invention (hereinafter referred to as group I) (in Column Co. 1) and as component 2) (in Column Co. 2) one pesticide from groups A) to O) [which is coded e.g. as (A.1.1) for azoxystrobin as defined above]

| Mixt. | Co. 1 | Co. 2 |
|---|---|---|
| B-777 | (I) | (L.5.43) |
| B-778 | (I) | (L.5.44) |
| B-779 | (I) | (L.5.45) |
| B-780 | (I) | (L.5.46) |
| B-781 | (I) | (L.5.47) |
| B-782 | (I) | (L.5.48) |
| B-783 | (I) | (L.5.49) |
| B-784 | (I) | (L.5.50) |
| B-785 | (I) | (L.5.51) |
| B-786 | (I) | (L.5.52) |
| B-787 | (I) | (L.5.53) |
| B-788 | (I) | (L.5.54) |
| B-789 | (I) | (L.5.55) |
| B-790 | (I) | (L.5.56) |
| B-791 | (I) | (L.5.57) |
| B-792 | (I) | (L.5.58) |
| B-793 | (I) | (L.5.59) |
| B-794 | (I) | (L.5.60) |
| B-795 | (I) | (L.6.1) |
| B-796 | (I) | (L.6.2) |
| B-797 | (I) | (L.6.3) |
| B-798 | (I) | (L.6.4) |
| B-799 | (I) | (L.6.5) |
| B-800 | (I) | (L.6.6) |
| B-801 | (I) | (L.6.7) |
| B-802 | (I) | (L.6.8) |
| B-803 | (I) | (L.6.9) |
| B-804 | (I) | (L.6.10) |
| B-805 | (I) | (L.6.11) |
| B-806 | (I) | (L.6.12) |
| B-807 | (I) | (L.6.13) |
| B-808 | (I) | (L.6.14) |
| B-809 | (I) | (L.6.15) |
| B-810 | (I) | (L.6.16) |

The active substances referred to as component 2, their preparation and their activity e.g. against harmful fungi is known; these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, PCT/EP2012/065650 and PCT/EP2012/065651).

The mixtures of active substances can be prepared as compositions comprising besides the active ingredients at least one inert ingredient (auxiliary) by usual means, e. g. by the means given for the compositions of the strains, cell-free extracts, culture media or extrolites of the invention.

One embodiment of the invention is a kit for preparing a usable pesticidal composition, the kit compring a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Concerning usual ingredients of such compositions reference is made to the explanations given for the compositions containing the strains, cell-free extracts, culture media or extrolites of the invention.

The mixtures to the invention are suitable as fungicides, as are the strains, cell-free extracts, culture media or extrolites of the invention. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is refered to the explanations regarding the fungicidal activity of the strains, cell-free extracts, culture media or extrolites of the invention.

The present invention will be described in greater detail by means of the following examples. The following examples are for illustrative purposes and are not intended to limit the scope of the invention.

EXPERIMENTAL PART

Optical rotation was measured on a Perkin Elmer polarimeter model 241 at 545 and 578 nm and was extrapolated to 589 nm using Drude's equation [Lippke, G.; Thaler, H. Starch 1970, 22, 344-351]. $^1$H, $^{13}$C and 2D NMR spectra were recorded on a Bruker AVANCE III 600 MHz spectrometer equipped with a 5 mm TCI cryogenic inverse probe head (z-gradient) using standard pulse sequences. APCI-MS spectra were measured from a solution of the analyte in MeCN/H$_2$0 with a Hewlett Packard MSD 1100 using an evaporator temperature of 400° C., a drying gas temperature of 350° C. at a flow of 6 L/h (N$_2$). In positive ionization mode, the capillary voltage amounted to 3.5 kV, the corona discharge current was 4 µA. In negative ionization mode, the capillary voltage amounted to 2.2 kV, the corona discharge current was 6 µA. HR-ESI-MS data were recorded on a Q-ToF ULTIMA-111 (Waters) equipped with a LockSpray-interface. A Bruker IFS48 FTIR spectrometer and a Perkin-Elmer Lambda-16 spectrophotometer were used to measure the IR and UV spectra, respectively.

Example 1

Isolation and Deposit of Fungal Strain IBWF104-06

The fungus IBWF104-06 was isolated from a soil sample. Strain IBWF104-06 has been deposited under the Budapest Treaty with the culture collection of Leibniz Institute DSMZ-German Collection of Microorganisms and Cell Cultures, Braunschweig, Germany, and has been assigned deposit number DSM 27859.

For maintenance, the fungus was grown on agar slants on YMG agar (yeast extract 4.0 g/L, malt extract 10 g/L, glucose 10 g/L, the pH value was adjusted to 5.5 before autoclaving). Solid media contained 2.0% of agar.

Example 2

Morphological Analysis

The strain was determined to be a *Penicillium* species based on the following morphological observations:
  Colony diameter, 7 days, in mm: CYA approx. 25; CYA30° C. approx. 24; CYA37° C. no growth; MEA approx. 25; YES approx. 33.
  Good sporulation on CYA with grey green conidia, reverse in shades of créme.
  Good sporulation on YES, grey green conidia, reverse slightly yellow, all media: soluble pigment absent. Colonies on MEA grey green conidia. No reaction with Ehrlich test. Conidiophores symmetrically biverticillate, metulae 13-17×2.3-2.9 µm; phialides ampulliform, 8-10×2-3 µm; conidia smooth, broadly ellipsoidal, 2.0-2.5×2.3-3 µm.
  Distribution and ecology: This species has been isolated from a soil sample (Mehlinger Heide, Mehlingen, Germany).

Example 3

Phylogentic Analysis

The ITS sequence of the fungus IBWF104-06 (SEQ ID NO:1) is shown in FIG. 1, with the underlined parts of the sequence corresponding to the primers used (ITS-1F: CTTGGTCATTTAGAGGAAGTAA (SEQ ID NO:2); ITS-4: TCCTCCGCTTATTGATATGC (SEQ ID NO:3); ITS-4 reverse complement GCATATCAATAAGCGGAGGA(SEQ ID NO:4) [Gardes, M., and T. D. Bruns. 1993]. ITS primers with enhanced specificity for basidiomycetes - application to the identification of mycorrhizae and rusts. Mol. Ecol. 2: 113-118; White, T. J., T. Bruns, S. Lee, and J. W. Taylor. 1990. Amplification and direct sequencing of fungal ribosomal RNA genes for phylogenetics. Pp. 315-322 In: PCR Protocols: A Guide to Methods and Applications, eds. Innis, M. A., D. H. Gelfand, J. J. Sninsky, and T. J. White. Academic Press, Inc., New York].

The ITS-Sequence for IBWF104-06 consists of partial 18S rRNA (conserved), ITS1, 5.8S rRNA, ITS2, partial 28S rRNA (conserved), with the two spacers (ITS1, ITS2), including the 5.8S gene, usually being referred to as the ITS region; for taxonomy this sequence is described as universal fungal barcode sequence [Schoch, et al., Proceedings of the National Academy of Sciences of the United States of America, 109(16), 6241-6. doi:10.1073/pnas.1117018109].

The ITS GenBank sequences for *Penicillium steckii* strain CBS 122389, *Penicillium steckii* strain CBS 122388 and *Penicillium steckii* strain CBS 122390 were found to be 100% identical with the ITS sequence of IBWF104-06 (see the following alignments A-C). Further seven deposited sequences of *Penicillium steckii* strains were found to show identities between 99.8 and 99.4% with the ITS sequence of IBWF104-06 (see the following alignments D-J).

Pairwise Alignment A
Sequence 1: 104-06 ITS
Sequence 2: gi|310769718|gb|GU944592.1| *Penicillium steckii* strain CBS 122389 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1090
Identity: 1,0000000
Pairwise Alignment B
Sequence 1: 104-06 ITS
Sequence 2: gi|310769717|gb|GU944591.1| *Penicillium steckii* strain CBS 122388 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1090
Identity: 1,0000000
Pairwise Alignment C
Sequence 1: 104-06 ITS
Sequence 2: gi|310769716|gb|GU944590.1| *Penicillium steckii* strain CBS 122390 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1090
Identity: 1,0000000
Pairwise Alignment D
Sequence 1: 104-06 ITS
Sequence 2: gi|74135519|gb|DQ123665.1| *Penicillium steckii* strain NRRL 35367 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1087

Identity: 0,9981685
Pairwise Alignment E
Sequence 1: 104-06 ITS
Sequence 2: gi|310769723|gb|GU944597.1| *Penicillium steckii* strain CBS 260.55 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1087
Identity: 0,9981651
Pairwise Alignment F
Sequence 1: 104-06 ITS
Sequence 2: gi|74135520|gb|DQ123666.1| *Penicillium steckii* strain NRRL 354633 18S ribosomal RNA gene, partial sequence; internal transcribed spacer 1, 5.8S ribosomal RNA gene, and internal transcribed spacer 2, complete sequence; and 28S ribosomal RNA gene, partial sequence >gi|156891115|gb|EF634431.1| *Penicillium steckii* isolate NRRL 35463 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1084
Identity: 0,9963303
Pairwise Alignment G
Sequence 1: 104-06 ITS
Sequence 2: gi|310769721|gb|GU944595.1| *Penicillium steckii* strain CBS 789.70 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1084
Identity: 0,9963303
Pairwise Alignment H
Sequence 1: 104-06 ITS
Sequence 2: gi|310769720|gb|GU944594.1| *Penicillium steckii* strain CBS 325.59 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1084
Identity: 0,9963303
Pairwise Alignment I
Sequence 1: 104-06 ITS
Sequence 2: gi|310769719|gb|GU944593.1| *Penicillium steckii* strain CBS 122391 18S ribosomal RNA gene, partial sequence; internal transcribed spacer 1, 5.8S ribosomal RNA gene, and internal transcribed spacer 2, complete sequence; and 28S ribosomal RNA gene, partial sequence
Optimal Global aligment
Alignment score: 1084
Identity: 0,9963303
Pairwise Alignment J
Sequence 1: 104-06 ITS
Sequence 2: gi|141452972|gb|EF200085.1| *Penicillium steckii* isolate NRRL 35625 internal transcribed spacer 1, 5.8S ribosomal RNA gene, and internal transcribed spacer 2, complete sequence; and 28S ribosomal RNA gene, partial sequence
Optimal Global aligment
Alignment score: 1081
Identity: 0,9945055

Thus, based on ITS sequence comparison, the fungus IBWF104-06 is a *Penicillium steckii* strain.

Example 4

Cultivation of *Penicillium steckii* Strain IBWF104-06

*Penicillium stecki* strain IBWF 104-06 was cultivated on 2% malt solid media for 3-4 days at RT. Spores were washed up using 2% malt liquid media and filtrated through GAZE. Spores were counted using haemocytometer and adjusted to about $1 \times 10^8$ cfu/ml.

Example 5

Antifungal Activity of *Penicillium steckii* Strain IBWF104-06

To test antifungal activity against *Phytophthora infestans, Botrytis cinerea* and *Alternaria solani*, commercially available young tomato seedlings ("Goldene Königin") were used for the described greenhouse trial. 2 replications (pots with 1 plant each) were used per treatment. Plants were grown in commercially available substrate (Universal, Floragard) at about 22° C. in the greenhouse. The humidity was controlled using a special device (~90% humidity). The plants were sprayed to runoff with crude culture broth of 3-6 days old cultures of *Penicillium steckii* strain IBWF104-06 using a spray cabinet. Culture conditions were as described in Example 4. One day after application the treated plants were inoculated with a suspension of i) sporangia of *Phytophthora infestans*, ii) spores of *Botrytis cinerea* or iii) spores of *Alternaria solani*. After inoculation, the trial plants were immediately transferred to a humid chamber. The extent of fungal attack on the leaves was visually assessed 5-7 days after inoculation.

For testing the antifungal activity against *Fusarium graminearum*, 8 week old plants of super dwarf wheat, commercially available young tomato seedlings ("Goldene Königin") and commercially available young pepper seedlings ("Neusiedler Ideal") were used for the described greenhouse trial. 2 replications were used per treatment. Plants were grown in commercially available substrate (Universal, Floragard) at about 21-22° C. in the greenhouse. The humidity was controlled using a special device (~60%-90% humidity depending on the pathogen). The plants were sprayed with conidia suspensions of 7 day old cultures of *Penicillium steckii* strain IBWF104-06 using a spray cabinet. One day after application the treated plants were inoculated with a conidia suspension of i) sporangia of *Phytophthora infestans*, ii) spores of Botrytis cinerea or iii) spores of *Alternaria solani* iiii) spores of *Fusarium graminearum*. After inoculation, the trial plants were immediately transferred to a humid chamber. The extent of fungal attack on the leaves was visually assessed 5-7 days after inoculation.

TABLE 1

Fungicidal activity - Percent infestation

% attack (UTC set to 100%)

| | BOTRCI | ALTESO | PHYTIN | FUSAGR | CFU/ml |
|---|---|---|---|---|---|
| *Penicillium steckii* strain IBWF 104-06 | 1 | 9 | 13 | | 1.0E+08 |
| *Penicillium steckii* strain IBWF 104-06 | | | | 0 | 8.16E+07 |

% attack

| | BOTRCI | ALTESO | PHYTIN | FUSAGR |
|---|---|---|---|---|
| UTC | 100 | 42.5 | 95 | 76.3 |
| *Penicillium steckii* strain IBWF 104-06 | 1 | 4 | 12.5 | 0 |

PHYTIN *Phytophthora infestans*
BOTRCI *Botrytis cinerea*
ALTESO *Alternaria solani*
FUSAGR *Fusarium graminearum*

Example 6

Growth (Fermentability) of Strains and Isolation of Tanzawaic Acids

*Penicillium steckii* strain IBWF 104-06 was grown in YMG medium in a 20 L-fermenter (Braun, Melsungen) at 22-24° C. with agitation (120 rpm) and aeration (3 L/min). For inoculation a well-grown shake culture (YMG medium, 250 mL) was used. During fermentation, the bioactive principles were quantified by HPLC and 13 days after inoculation the production was pronounced and the fermentation was stopped. The culture fluid (14.5 L) was separated from the mycelium by filtration and extracted with ethyl acetate (10 L). The solvent was evaporated and the oily crude extract (2.2 g) was applied onto a column filled with silica gel (Merck 60, 0.063-0.2 mm). Elution with a mixture of cyclohexane/ethyl acetate (3:2 v/v) yielded the oily fraction 1 (700 mg), 2:3 cyclohexane/ethyl acetate eluted oily fraction 2 (560 mg), and 1:4 cyclohexane/ethyl acetate eluted oily fraction 3 (100 mg). Further workup of fraction 1 by solid phase extraction with 1:1 acetonitrile/water generated intermediate A (600 mg), and with 1:4 acetonitrile/water intermediate B (50 mg). Preparative HPLC with intermediate A (Waters SunFire, Prep C18 OBD, 5 μm, 19×250 mm, 17 mL/min, isocratic conditions, 1:1 acetonitrile/0.1% formic acid) resulted in arohynapene A (173 mg, RT 9 min) and tanzawaic acid E (143 mg, RT 13 min). Intermediate B yielded tanzawaic acid A (7, 20 mg, RT 24 min) by preparative HPLC (Waters SunFire, Prep C18 OBD, 5 μm, 19×250 mm, 17 mL/min, isocratic conditions, 13:7 acetonitrile/0.1% formic acid). Work-up of fraction 2 by preparative HPLC (Waters SunFire, Prep C18 OBD, 5 μm, 19×250 mm, 17 mL/min, isocratic conditions, 11:9 acetonitrile/0.1% formic acid) generated the compound of formula (3) (termed tanzawaic acid K; 54 mg, RT 16.5 min) and intermediate C (RT 7-13 min, 320 mg). Intermediate C yielded the compound of formula (4) (termed tanzawaic acid L, 29 mg, RT 25.5 min) and arohynapene B (14 mg, RT 31 min) by a second preparative HPLC (Agilent PrepHT, Zorbax, XDB-C8, 21.2×150 mm, 5 μm, 21 mL/min, isocratic conditions, 7:13 acetonitrile/0.1% formic acid). Fraction 3 was applied onto a solid phase extraction column (Macherey-Nagel, Chromabond C18ec) and extraction with 2:3 acetonitrile/0.1% formic acid gave intermediate D (87 mg) which was used for preparative HPLC (Waters SunFire, Prep C18 OBD, 5 μm, 19×250 mm, 16 mL/min, isocratic conditions, 2:3 acetonitrile/0.1% formic acid) to yield the compound of formula (1) (termed tanzawaic acid I; 7.7 mg, RT 9 min) and the compound of formula (2) (termed tanzawaic acid J; 12.6 mg, RT 10.5 min).

Tanzawaic acid I: formula (1); Yellow oil; UV (MeOH) ($\lambda_{max}$, log ε): 261 (4.45); $[\alpha]_D^{20}$ −262 (0.4, MeOH); IR (v cm$^{-1}$) 3414, 2950, 2923, 1689, 1640, 1457, 1380, 1248; HR-ESI-MS: m/z 329.1744 (calc. for 329.1729 [$C_{18}H_{26}O_4$+Na]$^+$); APCI-MS (neg) m/z 305.1 [M−H]$^-$, APCI-MS (pos) 289.2 [M−H$_2$O+H]$^+$, 271.2 [M−2H$_2$O+H]$^+$.

Tanzawaic acid J: formula (2); Yellow oil; UV (MeOH) ($\lambda_{max}$, log ε): 261 (4.45); $[\alpha]_D^{20}$ +73.7 (0.4, MeOH); IR (v cm$^{-1}$) 3369, 2947, 2835, 1638, 1451, 1032; HR-ESI-MS: m/z 329.1744 (calc. for 329.1729 [$C_{18}H_{26}O_4$+Na]$^+$); APCI-MS negative mode m/z 305.1 [M−H]$^-$, APCI-MS positive mode 289.2 [M−H$_2$O+H]$^+$, 271.2 [M−2H$_2$O+H]$^+$.

Tanzawaic acid K: formula (3); Yellow oil; UV (MeOH) ($\lambda_{max}$, log ε): 257 (4.59); $[\alpha]_D^{20}$ −20.1 (0.38, MeOH); IR (v cm$^{-1}$) 3432, 2909, 1688, 1638, 1456, 1275; HR-ESI-MS: m/z 313.1788 (calc. for 313.1780 [$C_{18}H_{26}O_4$+Na]$^+$); APCI-MS (neg) m/z 289.1 [M−H]$^-$, APCI-MS (pos) 273.2 [M−H$_2$O+H]$^+$.

Tanzawaic acid L: formula (4); Yellow oil; UV (MeOH) ($\lambda_{max}$, log ε): 255 (3.70), 286 (3.68); $[\alpha]_D^{20}$ −126.7 (0.32, MeOH); IR (v cm$^{-1}$) 3409, 2961, 2965, 1698, 1638, 1377, 1247; HR-ESI-MS: m/z 311.1630 (calc. for 311.1623 [$C_{18}H_{26}O_4$+Na]$^+$); APCI-MS (neg) m/z 287.1 [M−H]$^-$, APCI-MS (pos) 271.1 [M−H$_2$O+H]$^+$, 253.1 [M−2H$_2$O+H]$^+$.

TABLE 2

$^1$-H-NMR data of the compounds of formula (1)-(4) (CD$_3$OD, 600 MHz)

| Position | Compound (1) | Compound (2) | Compound (3) | Compound (4) |
|---|---|---|---|---|
| 1 | — | — | — | — |
| 2 | 5.86 (1H, d, 15.3) | 5.83 (1H, d, 15.3) | 5.80 (1H, d, 15.3) | 5.87 (1H, d, 15.1) |
| 3 | 7.28 (1H, dd, 11.2, 15.3) | 7.28 (1H, dd, 11.2, 15.3) | 7.32 (1H, dd, 10.9, 15.3) | 7.37 (1H, dd, 11.1, 15.1) |
| 4 | 6.45 (1H, dd, 11.2, 15.2) | 6.45 (1H, dd, 11.2, 15.5) | 6.20 (1H, dd, 11.0, 15.0) | 6.33 (1H, dd, 11.1, 15.6) |
| 5 | 6.10 (1H, d, 15.2) | 6.16 (1H, d. 15.5) | 6.31 (1H, dd, 10.6, 15.0) | 6.74 (1H, d, 15.6) |
| 6 | — | — | 2.40 (1H, t, 10.6)- | — |

TABLE 2-continued

¹-H-NMR data of the compounds of formula (1)-(4) (CD₃OD, 600 MHz)

| Position | Compound (1) | Compound (2) | Compound (3) | Compound (4) |
|---|---|---|---|---|
| 7 | 1.39 (1H, m) | 1.52 (1H, d, 11.0) | 1.09 (1H, m) | 1.56 (1H, m) |
| 8 | 1.39 (1H, m) | 1.75 (1H, m) | 1.39 (1H, m) | 2.03 (1H, m) |
| 9 | 0.72 (1H$_\beta$, q, 11.8) 1.54 (1H$_\alpha$, m) | 0.78 (1H$_\beta$, q, 12.3) 1.57 (1H$_\alpha$, m) | 0.77 (1H$_\beta$, m) 1.65 (1H$_\alpha$, pseudo-dd, 3.1, 13.3) | 1.06 (1H$_\beta$, dd, 11.9, 13.9) 1.73 (1H$_\alpha$, m) |
| 10 | 1.45 (1H, d, 6.6) | 1.50 (1H, m) | 1.54 (1H, m) | — |
| 11 | 1.17 (1H$_\beta$, q, 12.3) 1.54 (1H$_\alpha$, m) | 1.17 (1H$_\beta$, q, 12.4) 1.56 (1H$_\alpha$, m) | 0.72 (1H$_\beta$, m) 1.71 (1H$_\alpha$, pseudo-dd, 3.0, 13.0) | 1.33 (1H$_\beta$, t, 13.3) 1.69 (1H$_\alpha$, m) |
| 12 | 1.59 (1H, m) | 1.61 (1H, m) | 1.94 (1H, pseudo-t, 11.0) | 2.36 (1H, m) |
| 13 | 3.80 (1H, t, 4.4) | 3.75 (1H, dd., 2.7, 5.8) | 5.41 (1H, d, 10.0) | 5.74 (1H, dd, 2.2, 9.2) |
| 14 | 5.69 (1H; d, 5.2) | 5.79 (1H, d, 6.1) | 5.48 (1H, dd, 2.4, 10.0) | 5.97 (1H, dd, 2.8, 9.2) |
| 15 | — | — | — | — |
| 16 | 1.62 (3H, s) | 1.63 (3H, s) | 1.18 (3H, s) | 1.89 (3H, s) |
| 17 | 0.90 (3H, d, 6.4) | 0.91 (3H, d, 6.4) | 0.89 (3H, d, 6.5) | 1.20 (3H, s) |
| 18 | 1.09 (3H, d, 5.3) | 0.91 (3H, d, 6.4) | 0.98 (3H, d, 6.3) | 0.98 (3H, d. 6.2) |

TABLE 3

¹³C-NMR data of compounds of formula (1)-(4) (CD₃OD, 150 MHz)

| Position | Compound (1) | Compound (2) | Compound (3) | Compound (4) |
|---|---|---|---|---|
| 1 | 170.9 | 170.9 | 170.9 | 170.9 |
| 2 | 122.0 | 121.3 | 120.6 | 120.8 |
| 3 | 145.9 | 146.2 | 146.7 | 147.1 |
| 4 | 128.5 | 127.8 | 130.5 | 131.0 |
| 5 | 144.8 | 153.7 | 147.5 | 142.3 |
| 6 | 79.0 | 76.1 | 58.8 | 133.4 |
| 7 | 49.8 | 49.1 | 51.1 | 49.9 |
| 8 | 35.3 | 34.3 | 37.2 | 29.1 |
| 9 | 47.1 | 47.1 | 48.1 | 49.3 |
| 10 | 32.9 | 33.0 | 33.7 | 70.1 |
| 11 | 39.1 | 39.0 | 42.8 | 44.0 |
| 12 | 41.4 | 39.9 | 44.7 | 35.9 |
| 13 | 67.6 | 68.0 | 132.9 | 137.3 |
| 14 | 127.0 | 128.0 | 135.2 | 131.0 |
| 15 | 142.9 | 140.9 | 74.5 | 133.8 |
| 16 | 18.1 | 19.1 | 24.6 | 19.8 |
| 17 | 23.1 | 23.1 | 22.8 | 31.3 |
| 18 | 23.0 | 24.2 | 23.8 | 23.4 |

Example 7

Determination of in vitro Activity of the Isolated Compounds

Antimicrobial activities of the isolated compounds against bacteria and fungi were determined in the agar plate diffusion assay as described previously [Anke, H.; Bergendorff, 0.; Sterner, 0 . Food Chem. Toxicol. 1989, 27, 393-397]. Cytotoxicity was assayed as described previously [Zapf, S.; Hossfeld, M.; Anke, H.; Velten, R.; Steglich, W. J. Antibiot. 1995, 48, 36-41]. The cell line HelaS3 was grown in DMEM medium (Invitrogen). The medium was supplemented with 10% heat-inactivated fetal calf serum (Invitrogen), 65 mg/mL of penicillin G and 100 mg/mL of streptomycin sulfate. The viability was evaluated by eye after 72 h. The spore gemination was tested with *Magnaporthe olyzae* as described previously [Kettering, M.; Valdivia, C.; Sterner, O.; Anke, H.; Thines, E. J. Antibiot. 2005, 58, 390-396]. This method was adapted for the spore germination assay with *Phytophthora infestans* and *Botrytis cinerea*.

It was found that apart from tanzawaic acid I and J, all isolated compounds (including tanzawaic acid K and L) inhibited the conidial spore germination of *Magnaporthe olyzae* with concentrations of 50 µg/mL or less whereas the germination of the grey mold *Botrytis cinerea* and the potato blight causing oomycete *Phytophora infestans* was not inhibited up to 50 µg/mL. Arohynapenes A and B inhibited the spore germination of *Magnaporthe oryzae* at 25 µg/mL (100%). In addition tanzawaic acid A showed slight activity in agar diffusion assays at 50 µg/filter against *Bacillus brevis, Mucor miehei,* and *Paealomyces variotii,* as well as cytotoxic effects against HeLaS3 cells at a concentration of 50 µg/mL. However, none of the other compounds showed bioactivity in these assays up to 50 µg/mL.

Example 8

Production of Tanzawaic Acids on Different Media

*Penicillium steckii* IBWF 104-06 was grown in four media and evaluated for tanzawaic acids production.

It was cultivated as described in Example 6 using the following media:
YMG medium (4 g/l yeast extract, 10 g/l malt extract, 10 g/l glucose, pH 5.5),
YM medium (4 g/l yeast extract, 10 g/l malt extract, 4 g/l glucose, pH 5.5),
DM medium (40 g/l malt extract, pH 5.5) and
PDA medium (24 g/l Difco Potato Dextrose Broth).

In addition to room temperature cultivation was also carried out at 27° C.

Tanzawaic acids were then extracted from each the media using the protocol of Example 6.

It was found that *Penicillium steckii* strain IBWF 104-06 produced the tanzawaic acids in each of the tested media.

All documents cited herein are incorporated by reference

The invention claimed is:

1. A method of controlling plant pathogens, suppressing plant pathogens or preventing plant pathogen infection, comprising:
contacting the plant pathogen, a plant to be protected from pathogen infection, or plant propagation material with an effective amount of a cell-free extract of *Penicillium:*
strain IBWF104-06 as deposited with DSMZ under the deposit number DSM 27859;

wherein the cell-free extract comprises one or more of said tanzawaic acids (1)-(4):

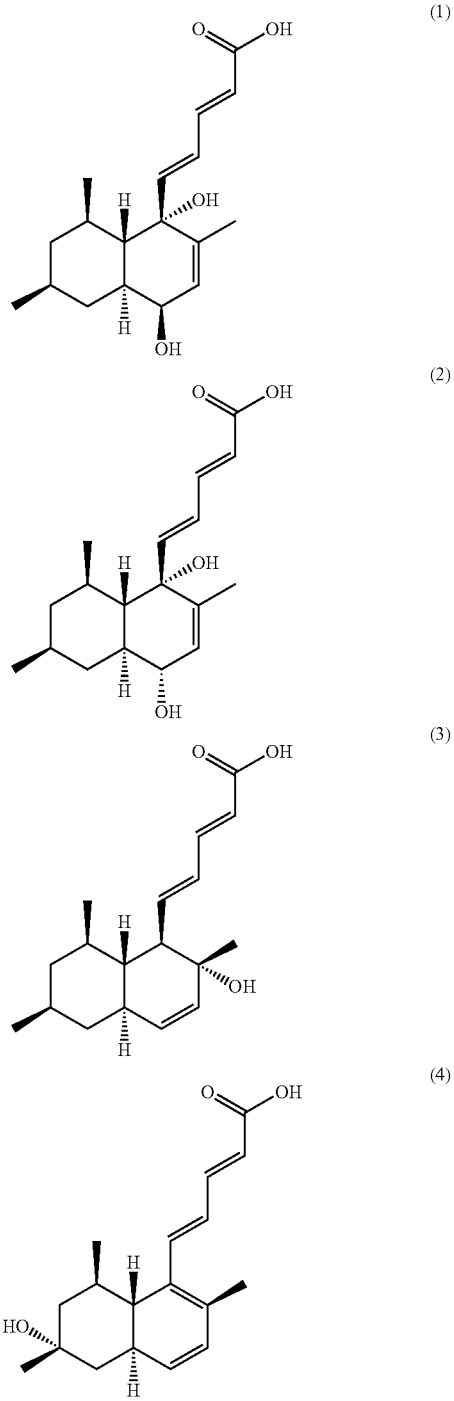

or an agriculturally acceptable salt thereof.

2. A method of controlling plant pathogens, suppressing plant pathogens or preventing plant pathogen infection, comprising:
contacting the plant pathogen, a plant to be protected from pathogen infection, or plant propagation material with an effective amount of a culture medium obtained by culturing *Penicillium* strain IBWF104-06 as deposited with DSMZ under the deposit number DSM 27859 in a culture medium and separating the medium from the culture broth, wherein the culture medium comprises one or more of the following tanzawaic acids:

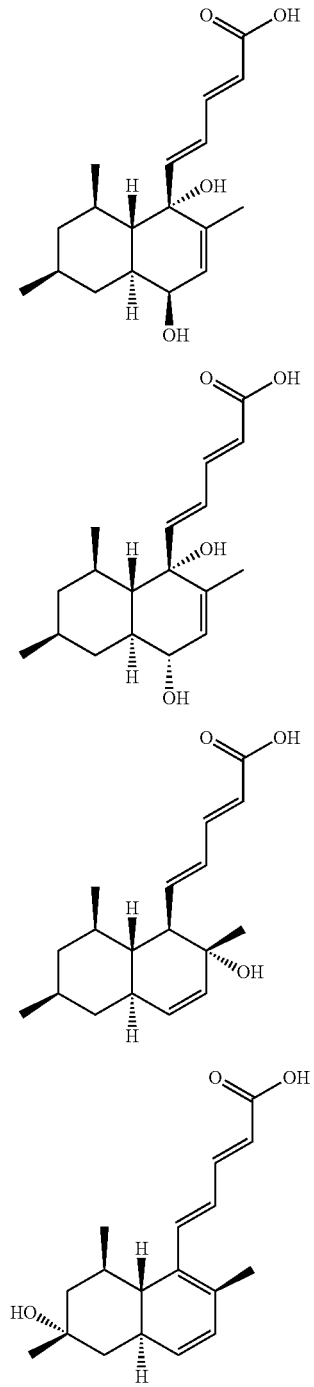

or an agriculturally acceptable salt thereof.

3. A method of controlling plant pathogens, suppressing plant pathogens or preventing plant pathogen infection, comprising:

contacting the plant pathogen, a plant to be protected from pathogen infection, or plant propagation material with an effective amount of a composition comprising a tanzawaic acid of formula (1), (2), (3) or (4):

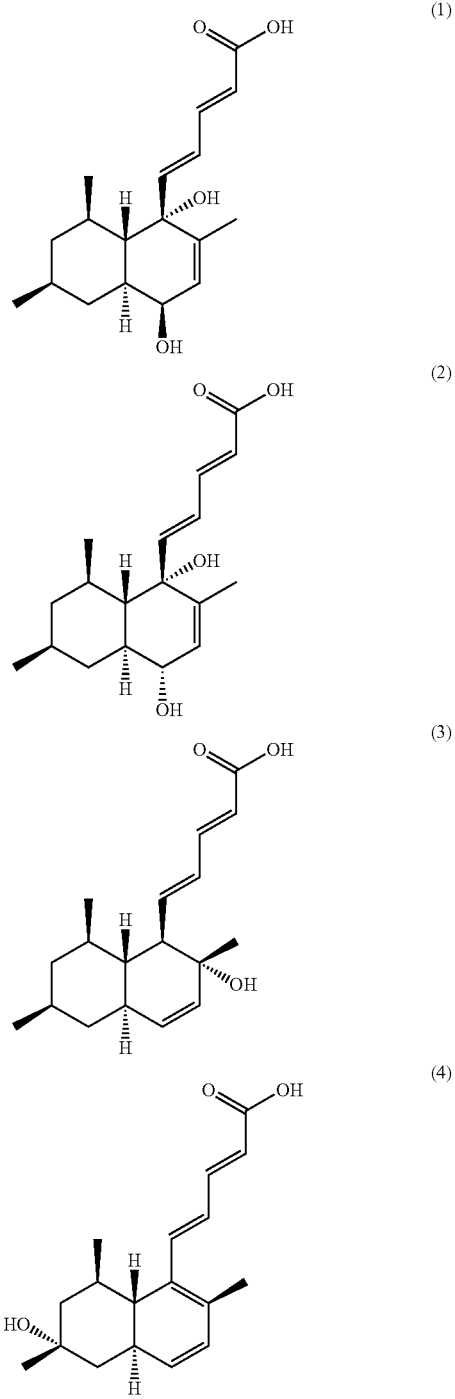

or an agriculturally acceptable salt thereof, wherein the composition is in the form of a powder, an emulsion, a suspension, a solution, a granule, a gel, or a microcapsule.

4. A method of controlling plant pathogens, suppressing plant pathogens or preventing plant pathogen infection, comprising:

contacting the plant pathogen, a plant to be protected from pathogen infection, or plant propagation material with an effective amount of an isolated tanzawaic acid of formula (1), (2), (3) or (4):
(1)
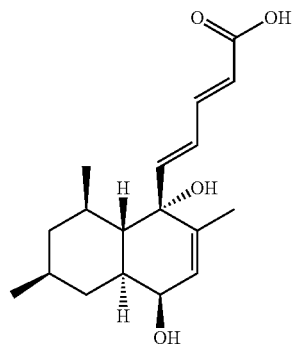
(2)
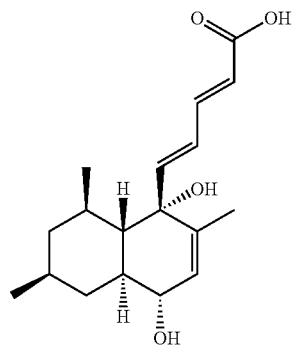
(3)
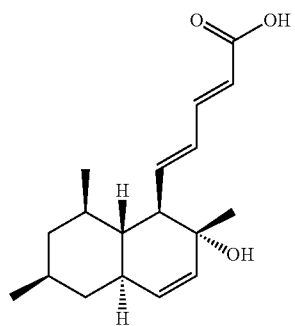
(4)
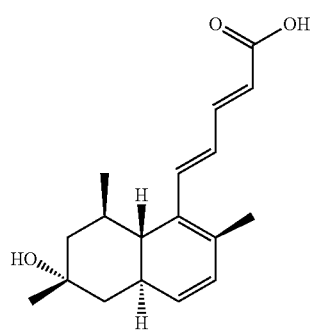
or an agriculturally acceptable salt thereof, wherein said tanzawaic acid is isolated from a culture broth comprising *Penicillium* strain IBWF104-06 as deposited with DSMZ under the deposit number DSM 27859.
* * * * *

SEQUENCE LISTING

<160> NUMBER OF SEQ ID NOS: 4

<210> SEQ ID NO 1
<211> LENGTH: 624
<212> TYPE: DNA
<213> ORGANISM: Penicillium steckii

<400> SEQUENCE: 1

| | | | | |
|---|---|---|---|---|
| cttggtcatt tagaggaagt aaaagtcgta acaaggtttc cgtaggtgaa cctgcggaag | | | | 60 |
| gatcattacc gagtgagggc cctctgggtc caacctccca cccgtgttgc acgaacctgt | | | | 120 |
| gttgcttcgg cgggcccgcc gccaggccgc cgggggcat ccgccccgg gtccgcgccc | | | | 180 |
| gccgaagccc ccctctgaac gctgtctgaa gttgcagtct gagacaacta gctaaattag | | | | 240 |
| ttaaaacttt caacaacgga tctcttggtt ccggcatcga tgaagaacgc agcgaaatgc | | | | 300 |
| gataactaat gtgaattgca gaattcagtg aatcatcgag tctttgaacg cacattgcgc | | | | 360 |
| cctctggtat tccggagggc atgcctgtcc gagcgtcatt gctgccctca agcacggctt | | | | 420 |
| gtgtgttggg ccccgtcccc cccgctccgg gggggacggg cccgaaaggc agcggcggca | | | | 480 |
| ccgcgtccgg tcctcgagcg tatggggctt cgtcacccgc tcttgtaggc ccggccggcg | | | | 540 |
| ccagccgacc cccaaccttt tatttttct caggttgacc tcggatcagg tagggatacc | | | | 600 |
| cgctgaactt aagcatatca ataa | | | | 624 |

<210> SEQ ID NO 2
<211> LENGTH: 22
<212> TYPE: DNA
<213> ORGANISM: Penicillium steckii

<400> SEQUENCE: 2
cttggtcatt tagaggaagt aa                                             22

<210> SEQ ID NO 3
<211> LENGTH: 20
<212> TYPE: DNA
<213> ORGANISM: Penicillium steckii

<400> SEQUENCE: 3
tcctccgctt attgatatgc                                                20

<210> SEQ ID NO 4
<211> LENGTH: 20
<212> TYPE: DNA
<213> ORGANISM: Penicillium steckii

<400> SEQUENCE: 4
gcatatcaat aagcggagga                                                20